(12) United States Patent
Hobbs et al.

(10) Patent No.: US 9,109,089 B2
(45) Date of Patent: *Aug. 18, 2015

(54) MULTIFUNCTIONAL SULFUR-CONTAINING POLYMERS, COMPOSITIONS THEREOF AND METHODS OF USE

(71) Applicant: PRC-DeSoto International, Inc., Sylmar, CA (US)

(72) Inventors: Steven J. Hobbs, Gilbert, AZ (US); Gregory J. McCollum, Gibsonia, PA (US); Juexiao Cai, Stevenson Ranch, CA (US); Marfi Ito, Culver City, CA (US); Lawrence G. Anderson, Allison Park, PA (US); Renhe Lin, Stevenson Ranch, CA (US)

(73) Assignee: PRC-DeSoto International, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/656,743

(22) Filed: Mar. 13, 2015

(65) Prior Publication Data

US 2015/0183806 A1    Jul. 2, 2015

Related U.S. Application Data

(60) Continuation of application No. 14/499,293, filed on Sep. 29, 2014, which is a continuation of application No. 14/177,596, filed on Feb. 11, 2014, now Pat. No. 8,877,887, which is a division of application No. 13/413,143, filed on Mar. 6, 2012, now Pat. No. 8,729,216.

(60) Provisional application No. 61/453,978, filed on Mar. 18, 2011.

(51) Int. Cl.

| C08G 75/10 | (2006.01) |
| C08G 75/12 | (2006.01) |
| C08G 77/00 | (2006.01) |
| C09J 181/02 | (2006.01) |
| C08G 65/34 | (2006.01) |
| C07D 251/30 | (2006.01) |
| C08G 65/336 | (2006.01) |

(52) U.S. Cl.
CPC .............. *C08G 75/12* (2013.01); *C07D 251/30* (2013.01); *C08G 65/336* (2013.01); *C08G 65/34* (2013.01); *C08G 75/10* (2013.01); *C08G 77/00* (2013.01); *C09J 181/02* (2013.01)

(58) Field of Classification Search
CPC .... C07D 251/30; C08G 65/34; C08G 65/336; C08G 75/10; C08G 75/12; C08G 77/10; C09J 181/02

USPC ............................ 528/226, 265; 525/487, 535
See application file for complete search history.

(56) References Cited

U.S. PATENT DOCUMENTS

| 2,466,963 | A | 4/1949 | Patrick et al. |
| 3,136,830 | A | 6/1964 | Oertel et al. |
| 3,290,382 | A | 12/1966 | Hubscher et al. |
| 3,647,766 | A | 3/1972 | Bertozzi |
| 3,959,227 | A | 5/1976 | Chang et al. |
| 3,997,612 | A | 12/1976 | Lenke et al. |
| 3,997,613 | A | 12/1976 | Lenke et al. |
| 3,997,614 | A | 12/1976 | Lenke et al. |
| 4,124,645 | A | 11/1978 | Bertozzi |
| 4,209,426 | A | 6/1980 | Sarantakis |
| 4,366,307 | A | 12/1982 | Singh et al. |
| 4,609,762 | A | 9/1986 | Morris et al. |
| 5,225,472 | A | 7/1993 | Cameron et al. |
| 5,912,319 | A | 6/1999 | Zook et al. |
| 5,959,071 | A | 9/1999 | DeMoss et al. |
| 6,172,179 | B1 | 1/2001 | Zook et al. |
| 6,232,401 | B1 | 5/2001 | Zook et al. |
| 6,372,849 | B2 | 4/2002 | DeMoss et al. |
| 6,383,324 | B1 | 5/2002 | Vietti et al. |
| 6,509,418 | B1 | 1/2003 | Zook et al. |
| 6,875,800 | B2 | 4/2005 | Vanier et al. |
| 6,894,086 | B2 | 5/2005 | Munro et al. |
| 7,438,972 | B2 | 10/2008 | Faler et al. |
| 7,638,162 | B2 | 12/2009 | Cosman |
| 2005/0245695 | A1 | 11/2005 | Cosman |
| 2008/0199603 | A1 | 8/2008 | Cosman |
| 2010/0036063 | A1 | 2/2010 | Sawant et al. |
| 2010/0184899 | A1 | 7/2010 | Rao et al. |
| 2011/0092639 | A1 | 4/2011 | Rao et al. |

FOREIGN PATENT DOCUMENTS

| CN | 1798809 A | 7/2006 |
| CN | 101186683 A | 5/2008 |
| EP | 1103571 A2 | 5/2001 |
| EP | 1925628 A1 | 5/2008 |
| GB | 850178 | 9/1960 |
| GB | 1286394 | 8/1972 |
| JP | 08-259859 | 10/1996 |
| JP | 2004-502826 A | 1/2004 |
| JP | 2004-502827 A | 1/2004 |
| JP | 2006-524720 A | 11/2006 |
| JP | 2007-514819 A | 6/2007 |
| JP | 2008-514769 A | 5/2008 |
| JP | 2010-529279 A | 8/2010 |
| JP | 2014-515767 A | 7/2014 |
| WO | 2007/050725 A1 | 5/2007 |
| WO | 2012/129088 A1 | 9/2012 |

*Primary Examiner* — Randy Gulakowski
*Assistant Examiner* — Christopher M Rodd
(74) *Attorney, Agent, or Firm* — William R. Lambert

(57) ABSTRACT

Disclosed are multifunctional sulfur-containing polymers that are the reaction products of a sulfur-containing diol, a polyol containing at least three hydroxyl groups per polyol molecule, and an aldehyde, a ketone, or a combination thereof. Sealant compositions comprising the multifunctional sulfur-containing polymers are also disclosed.

23 Claims, No Drawings

MULTIFUNCTIONAL SULFUR-CONTAINING POLYMERS, COMPOSITIONS THEREOF AND METHODS OF USE

CROSS-REFERENCE TO RELATED APPLICATIONS

This application is a Continuation of U.S. application Ser. No. 14/499,293, filed on Sep. 29, 2014, which is a Continuation of U.S. application Ser. No. 14/177,596, filed on Feb. 11, 2014, now issued as U.S. Pat. No. 8,877,887, which is a Division of U.S. application Ser. No. 13/413,143, filed on Mar. 6, 2012, now issued as U.S. Pat. No. 8,729,216, which claims benefit under 35 U.S.C. §119(e) of U.S. Provisional Application No. 61/453,978, filed on Mar. 18, 2011; each of which is incorporated by reference in its entirety.

FIELD

The present disclosure relates to multifunctional sulfur-containing polymers, compositions comprising multifunctional sulfur-containing polymers, and methods of using multifunctional sulfur-containing polymers.

BACKGROUND

Thiol-terminated sulfur-containing polymers are known to be well-suited for use in various applications such as aerospace sealant compositions, due, in large part, to their fuel-resistance. Other desirable properties for aerospace sealant compositions include low temperature flexibility, short curing time (the time required to reach a predetermined strength), and elevated-temperature resistance, among others. Sealant compositions exhibiting at least some of these characteristics and containing thiol-terminated sulfur-containing polymers are described, for example, in U.S. Pat. Nos. 2,466,963, 4,366,307, 4,609,762, 5,225,472, 5,912,319, 5,959,071, 6,172,179, 6,232,401, 6,372,849, and 6,509,418. Polysulfides are also used in aerospace sealant applications where they provide high tensile strength, high shear strength, high-temperature thermal resistance, and fuel resistance, as disclosed, for example in U.S. Pat. No. 7,638,162 and U.S. Publication No. 2005/0245695.

Polythioethers that are liquid at room temperature and pressure and that have excellent low temperature flexibility and fuel resistance, such as those disclosed in U.S. Pat. No. 6,172,179, are also useful in aerospace sealant applications. For example, difunctional polythioethers having terminal hydroxyl groups prepared by reacting a hydroxyl compound with an aldehyde are described, in GB 850,178, U.S. Pat. Nos. 3,290,382, 3,959,227, and 3,997,614. Difunctional polythioethers terminated or capped with isocyanates are also known as disclosed, for example, in GB 850,178, and in U.S. Pat. Nos. 3,290,382, 3,959,227, and 3,997,614. Difunctional, i.e., linear, polythioethers, however, often swell upon prolonged exposure to hydrocarbon fuel and other lubricants. On the other hand, sealants made using polyfunctional polythioethers, can exhibit good fuel resistance, hardness and flexibility, but often with compromised adhesion and elongation.

It is desirable to provide polyfunctional polythioethers that are useful as fuel resistant and water resistant sealants with improved tensile strength and elongation, and without compromising adhesion.

SUMMARY

Multifunctional sulfur-containing polymers having enhanced properties suitable for aerospace sealant applications are provided.

In a first aspect of the present disclosure, terminal-modified sulfur-containing polymers are provided comprising the reaction products of reactants comprising: (a) a sulfur-containing diol; (b) a polyol containing at least three hydroxyl groups per polyol molecule; and (c) a reactant selected from an aldehyde, a ketone, and a combination thereof.

In a second aspect of the present disclosure, sulfur-containing polymers having the structure of Formula (I) are provided:

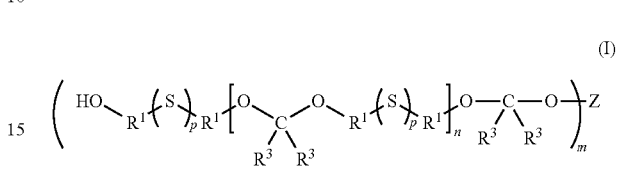

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$.

In a third aspect of the present disclosure, terminal-modified sulfur-containing polymers are provided comprising the reaction products of reactants comprising: (a) a sulfur-containing polymer of Formula (I):

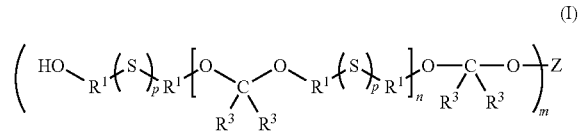

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (b) a compound comprising a terminal group selected from a vinyl group, a silyl group, an epoxy group, and an isocyanate group; and a group that is reactive with the hydroxyl groups of the polymer of Formula (I).

In a fourth aspect of the present disclosure, amine-terminated sulfur-containing polymers are provided comprising the reaction products of reactants comprising (a) and (b), wherein: (a) comprises the reaction products of reactants comprising (i) and (ii), wherein: (i) comprises a sulfur-containing polymer of Formula (I):

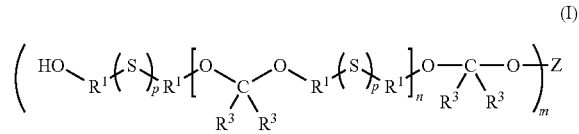

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (ii) comprises a first compound selected from a diisocyanate, an activated ethylenically unsaturated monoisocyanate, and a tosylate; and (b) comprises a second compound comprising an amine group and a group selected from a group that is reactive with an isocyanate group, a group that is reactive with an ethylenically unsaturated group, and a group that is reactive with a tosylate.

In a fifth aspect of the present disclosure, thiol-terminated sulfur-containing polymers are provided comprising the reaction products of reactants comprising (a) and (b), where (a) comprises the reaction products of reactants comprising (i) and (ii), wherein: (i) comprises a sulfur-containing polymer of Formula (I):

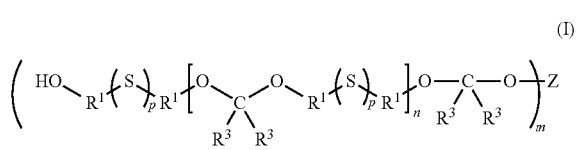

(I)

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (ii) comprises a first compound selected from a diisocyanate, thiourea, an ethylenically unsaturated monoisocyanate, and a tosylate; and (b) comprises a mercaptoalkanol when (ii) comprises a diisocyanate; a metal hydrosulfide when (ii) comprises thiourea; a dithiol when (ii) comprises an ethylenically unsaturated monoisocyanate; and a metal hydrosulfide when (ii) comprises a tosylate.

In a sixth aspect of the present disclosure, terminal-modified sulfur-containing polymers are provided comprising the reaction products of reactants comprising (a) and (b), wherein: (a) comprises the reaction products of reactants comprising (i) and (ii), where (i) comprises a sulfur-containing polymer of Formula (I):

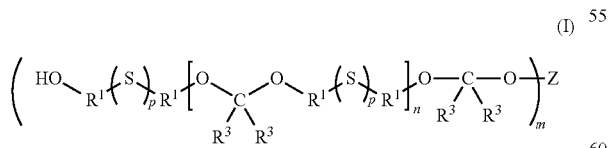

(I)

where n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (ii) comprises a first compound selected from a diisocyanate, an ethylenically unsaturated monoisocyanate, and a tosylate; and (b) comprises a second compound comprising a terminal group selected from a vinyl group, a silyl group, and an epoxy group; and a group selected from a group that is reactive with an isocyanate group, a group that is reactive with an ethylenically unsaturated group, and a group that is reactive with a tosylate. In a seventh aspect of the present disclosure, terminal-modified sulfur-containing polymers of Formula (II) are provided:

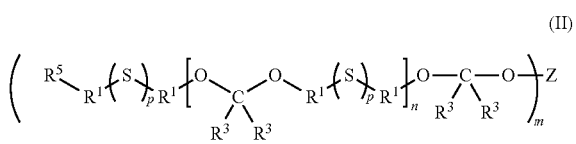

(II)

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; each $R^5$ is $-OR^{5'}$ wherein $R^{5'}$ is independently selected from a vinyl-terminated group, a silyl-terminated group, an amine-terminated group, an epoxy-terminated group, a thiol-terminated group, and an isocyanate-terminated group; and Z represents the core of an m-valent parent polyol $Z(OH)_m$.

In an eighth aspect of the present disclosure, compositions are provided comprising a terminal-modified sulfur-containing polymer provided by the present disclosure and a curing agent that is reactive with the terminal-modified sulfur-containing polymer.

In a ninth aspect of the present disclosure, apertures are provided that are sealed with a sealant comprising a composition comprising a terminal-modified sulfur-containing polymer provided by the present disclosure and a curing agent that is reactive with the terminal-modified sulfur-containing polymer.

The present disclosure is also directed to methods for making sulfur-containing polymers and compositions thereof, such as sealant compositions, including aerospace sealant compositions, comprising sulfur-containing polymers provided by the present disclosure.

DETAILED DESCRIPTION

Definitions

A dash ("-") that is not between two letters or symbols is used to indicate a point of bonding for a substituent or between two atoms. For example, $-CONH_2$ is bonded to another moiety through the carbon atom.

"Activated ethylenically unsaturated monoisocyanate" refers to a compound comprising an ethylenically unsaturated group and a monoisocyanate group in which the double bond is electron deficient such that it is activated toward Michael addition, i.e., the double bond is a Michael acceptor.

"Aldehyde" refers to a compound of the formula CH(O)R where R is hydrogen or a hydrocarbon group such as an alkyl group, as defined herein. In certain embodiments, the aldehyde is $C_{1-10}$ aldehyde, $C_{1-6}$ aldehyde, $C_{1-4}$ aldehyde, $C_{1-3}$ aldehyde, and in certain embodiments, $C_{1-2}$ aldehyde. In certain embodiments, the aldehyde is formaldehyde. In certain embodiments of the aldehyde, R is selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl.

"Alkanediyl" refers to a diradical of a saturated, branched or straight-chain, acyclic hydrocarbon group, having, for example, from 1 to 18 carbon atoms ($C_{1-18}$), from 1-14 carbon atoms ($C_{1-14}$), from 1-6 carbon atoms ($C_{1-6}$), from 1 to 4 carbon atoms ($C_{1-4}$), or from 1 to 3 hydrocarbon atoms ($C_{1-3}$). In certain embodiments, the alkanediyl is $C_{2-14}$ alkanediyl, $C_{2-10}$ alkanediyl, $C_{2-8}$ alkanediyl, $C_{2-6}$ alkanediyl, $C_{2-4}$ alkanediyl, and in certain embodiments, $C_{2-3}$ alkanediyl. Examples of alkanediyl groups include methane-diyl ($—CH_2—$), ethane-1,2-diyl ($—CH_2CH_2—$), propane-1,3-diyl and iso-propane-1,2-diyl (e.g., $—CH_2CH_2CH_2—$ and $—CH(CH_3)CH_2—$), butane-1,4-diyl ($—CH_2CH_2CH_2CH_2—$), pentane-1,5-diyl ($—CH_2CH_2CH_2CH_2CH_2—$), hexane-1,6-diyl ($—CH_2CH_2CH_2CH_2CH_2CH_2—$), heptane-1,7-diyl, octane-1,8-diyl, nonane-1,9-diyl, decane-1,10-diyl, dodecane-1,12-diyl, and the like.

"Alkanedithiol" refers to an alkane group in which two of the hydrogen atoms are replaced with a thiol group, $—SH$. In certain embodiments, the alkanedithiol is $C_{2-12}$ alkanedithiol, $C_{2-10}$ alkanedithiol, $C_{2-8}$ alkanedithiol, $C_{2-6}$ alkanedithiol, and in certain embodiments, $C_{2-3}$ alkanedithiol.

"Alkanearene" refers to a hydrocarbon group having one or more aryl and/or arenediyl groups and one or more alkyl and/or alkanediyl groups, where aryl, arenediyl, alkyl, and alkanediyl are defined here. In certain embodiments, each aryl and/or arenediyl group(s) is $C_{6-12}$, $C_{6-10}$, and in certain embodiments, phenyl or benzenediyl. In certain embodiments, each alkyl and/or alkanediyl group(s) is $C_{1-6}$, $C_{1-4}$, $C_{1-3}$, and in certain embodiments, methyl, methanediyl, ethyl, or ethane-1,2-diyl. In certain embodiments, the alkanearene group is $C_{4-18}$ alkanearene, $C_{4-16}$ alkanearene, $C_{4-12}$ alkanearene, $C_{4-8}$ alkanearene, $C_{6-12}$ alkanearene, $C_{6-10}$ alkanearene, and in certain embodiments, $C_{6-9}$ alkanearene. Examples of alkanearene groups include diphenyl methane.

"Alkanearenediyl" refers to a diradical of an alkanearene group. In certain embodiments, the alkanearenediyl group is $C_{4-18}$ alkanearenediyl, $C_{4-16}$ alkanearenediyl, $C_{4-12}$ alkanearenediyl, $C_{4-8}$ alkanearenediyl, $C_{6-12}$ alkanearenediyl, $C_{6-10}$ alkanearenediyl, and in certain embodiments, $C_{6-9}$ alkanearenediyl. Examples of alkanearenediyl groups include diphenyl methane-4,4'-diyl.

"Alkanecycloalkane" refers to a saturated hydrocarbon group having one or more cycloalkyl and/or cycloalkanediyl groups and one or more alkyl and/or alkanediyl groups, where cycloalkyl, cycloalkanediyl, alkyl, and alkanediyl are defined herein. In certain embodiments, each cycloalkyl and/or cycloalkanediyl group(s) is $C_{3-6}$, $C_{5-6}$, and in certain embodiments, cyclohexyl or cyclohexanediyl. In certain embodiments, each alkyl and/or alkanediyl group(s) is $C_{1-6}$, $C_{1-4}$, $C_{1-3}$, and in certain embodiments, methyl, methanediyl, ethyl, or ethane-1,2-diyl. In certain embodiments, the alkanecycloalkane group is $C_{4-18}$ alkanecycloalkane, $C_{4-16}$ alkanecycloalkane, $C_{4-12}$ alkanecycloalkane, $C_{4-8}$ alkanecycloalkane, $C_{6-12}$ alkanecycloalkane, $C_{6-10}$ alkanecycloalkane, and in certain embodiments, $C_{6-9}$ alkanecycloalkane. Examples of alkanecycloalkane groups include 1,1,3,3-tetramethylcyclohexane and cyclohexylmethane.

"Alkanecycloalkanediyl" refers to a diradical of an alkanecycloalkane group. In certain embodiments, the alkanecycloalkanediyl group is $C_{4-18}$ alkanecycloalkanediyl, $C_{4-16}$ alkanecycloalkanediyl, $C_{4-12}$ alkanecycloalkanediyl, $C_{4-8}$ alkanecycloalkanediyl, $C_{6-12}$ alkanecycloalkanediyl, $C_{6-10}$ alkanecycloalkanediyl, and in certain embodiments, $C_{6-9}$ alkanecycloalkanediyl. Examples of alkanecycloalkanediyl groups include 1,1,3,3-tetramethylcyclohexane-1,5-diyl and cyclohexylmethane-4,4'-diyl.

"Alkoxy" refers to a $—OR$ group where R is alkyl as defined herein. Examples of alkoxy groups include methoxy, ethoxy, n-propoxy, isopropoxy, and n-butoxy. In certain embodiments, the alkoxy group is $C_{1-8}$ alkoxy, $C_{1-6}$ alkoxy, $C_{1-4}$ alkoxy, and in certain embodiments, $C_{1-3}$ alkoxy.

"Alkyl" refers to a monoradical of a saturated, branched or straight-chain, acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. Examples of alkyl groups include methyl, ethyl, n-propyl, iso-propyl, n-butyl, iso-butyl, tert-butyl, n-hexyl, n-decyl, tetradecyl, and the like. In certain embodiments, the alkyl group is $C_{2-6}$ alkyl, $C_{2-4}$ alkyl, and in certain embodiments, $C_{2-3}$ alkyl.

"Aminoalkyl" refers to an alkyl group, as defined herein, in which one of the hydrogen atoms of the alkyl group is replaced with an amino group, $—NH_2$. In certain embodiments, the aminoalkyl group is $C_{1-10}$ aminoalkyl, $C_{1-6}$ aminoalkyl, $C_{1-4}$ aminoalkyl, $C_{1-3}$ aminoalkyl, and in certain embodiments, $C_{1-2}$ aminoalkyl.

"Arenediyl" refers to diradical monocyclic or polycyclic aromatic group. Examples of arenediyl groups include benzene-diyl and naphthalene-diyl. In certain embodiments, the arenediyl group is $C_{6-12}$ arenediyl, $C_{6-10}$ arenediyl, $C_{6-9}$ arenediyl, and in certain embodiments, benzene-diyl.

"Aryl" refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, the aryl group can have from 6 to 20 carbon atoms, and in certain embodiments, from 6 to 12 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein. In certain embodiments, an aryl group is phenyl.

"Arylalkyl" refers to an alkyl group in which one of the hydrogen atoms is replaced with an aryl group. In certain embodiments of an arylalkyl group, a hydrogen atom on the terminal carbon atom of an alkyl group is replaced with an aryl group. In certain embodiments of arylalkyl, the aryl group is a $C_{6-12}$ aryl group, in certain embodiments a $C_{6-10}$ aryl group, and in certain embodiments, a phenyl or naphthyl group. In certain embodiments, the alkanediyl portion of an arylalkyl group may be, for example, $C_{1-10}$ alkanediyl, $C_{1-6}$ alkanediyl, $C_{1-4}$ alkanediyl, $C_{1-3}$ alkanediyl, propane-1,3-diyl, ethane-1,2-diyl, or methane-diyl. In certain embodiments, the arylalkyl group is $C_{7-18}$ arylalkyl, $C_{7-16}$ arylalkyl, $C_{7-12}$ arylalkyl, $C_{7-10}$ arylalkyl, or $C_{7-9}$ arylalkyl. For example, $C_{7-9}$ arylalkyl can include a $C_{1-3}$ alkyl group bonded to a phenyl group.

"Cycloalkanediyl" refers to a diradical saturated monocyclic or polycyclic hydrocarbon group. In certain embodiments, the cycloalkanediyl group is $C_{3-12}$ cycloalkanediyl, $C_{3-8}$ cycloalkanediyl, $C_{3-6}$ cycloalkanediyl, and in certain embodiments, $C_{5-6}$ cycloalkanediyl. Examples of cycloalkanediyl groups include cyclohexane-1,4-diyl, cyclohexane-1,3-diyl, and cyclohexane-1,2-diyl.

"Cycloalkyl" refers to a saturated monocyclic or polycyclic hydrocarbon monoradical group. In certain embodiments, the cycloalkyl group is $C_{3-12}$ cycloalkyl, $C_{3-8}$ cycloalkyl, $C_{3-6}$ cycloalkyl, and in certain embodiments, $C_{5-6}$ cycloalkyl.

"Cycloalkylalkyl" refers to an alkyl group in which one of the hydrogen atoms is replaced with a cycloalkyl group. In certain embodiments of the cycloalkylalkyl group, a hydrogen atom on the terminal carbon atom of an alkyl group is replaced with a cycloalkyl group. In certain embodiments of cycloalkylalkyl, the cycloalkyl group is a $C_{3-6}$ cycloalkyl group, in certain embodiments a $C_{5-6}$ cycloalkyl group, and in certain embodiments, a cyclopropyl, a cyclobutyl, a cyclopentyl, or a cyclohexyl group. In certain embodiments, the alkanediyl portion of a cycloalkylalkyl group may be, for example, $C_{1-10}$ alkanediyl, $C_{1-6}$ alkanediyl, $C_{1-4}$ alkanediyl, $C_{1-3}$ alkanediyl, propane-1,3-diyl, ethane-1,2-diyl, or methane-diyl. In certain embodiments, the cycloalkylalkyl group is $C_{4-16}$ cycloalkylalkyl, $C_{4-12}$ cycloalkylalkyl, $C_{4-10}$ cycloalkylalkyl, $C_{6-12}$ cycloalkylalkyl, or $C_{6-9}$ cycloalkylalkyl. For example, $C_{6-9}$ cycloalkylalkyl includes a $C_{1-3}$ alkyl group bonded to a cyclopentyl or a cyclohexyl group.

"Cycloalkylalkanediyl" refers to a diradical of a cycloalkylalkane group. In certain embodiments, the cycloalkylalkanediyl group is $C_{4-16}$ cycloalkylalkanediyl, $C_{4-12}$ cycloalkylalkanediyl, $C_{4-10}$ cycloalkylalkanediyl, $C_{6-12}$ cycloalkylalkanediyl, or $C_{6-9}$ cycloalkylalkanediyl. For example, $C_{6-9}$ cycloalkylalkanediyl includes a $C_{1-3}$ alkyl group bonded to a cyclopentyl or a cyclohexyl group.

"Cycloalkylalkane" group refers to a saturated, branched or straight-chain, acyclic hydrocarbon group in which one of the hydrogen atoms is replaced with a cycloalkane group. In certain embodiments of the cycloalkylalkane group, a hydrogen atom on the terminal carbon atom of a linear alkane group is replaced with a cycloalkyl group. In certain embodiments the cycloalkyl group is a $C_{3-6}$ cycloalkyl group, in certain embodiments a $C_{5-6}$ cycloalkyl group, and in certain embodiments a cyclopropyl, a cyclobutyl, a cyclopentyl, or a cyclohexyl group. The alkane portion of a cycloalkylalkane group may be, for example, $C_{1-10}$ alkane, $C_{1-6}$ alkane, $C_{1-4}$ alkane, $C_{1-3}$ alkane, propane, ethane, or methane. In certain embodiments, a cycloalkylalkane group is $C_{4-16}$ cycloalkylalkane, $C_{4-12}$ cycloalkylalkane, $C_{4-10}$ cycloalkylalkane, $C_{6-12}$ cycloalkylalkane, or $C_{6-9}$ cycloalkylalkane. For example, $C_{6-9}$ cycloalkylalkane includes a $C_{1-3}$ alkyl group bonded to a cyclopentyl or a cyclohexyl group.

"Group derived from a diisocyanate" refers to a group in which one or both of the terminal isocyanate groups of a parent diisocyanate form a urethane (—O—C(O)—NR—), thiourethane (—S—C(O)—NR—), or urea (—NR—C(O)—NR—) linkage, where R is hydrogen or a hydrocarbon group. The group derived from a diisocyanate includes groups derived from aliphatic diisocyanates and groups derived from aromatic diisocyanates. In certain embodiments, the group derived from a diisocyanate is a group derived from an aliphatic diisocyanate, and in certain embodiments a group derived from a diisocyanate is a group derived from an aromatic diisocyanate. For example, a compound derived from 2,6-diisocyanatotoluene has the structure:

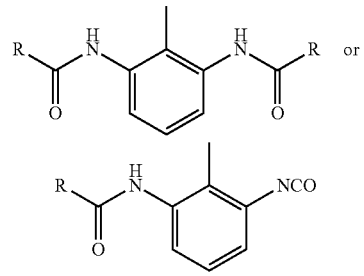

where each R is a bond to a —O—, —S—, or —NR— group.

Examples of aliphatic diisocyanates include, 1,6-hexamethylene diisocyanate, 1,5-diisocyanato-2-methylpentane, methyl-2,6-diisocyanatohexanoate, bis(isocyanatomethyl) cyclohexane, 1,3-bis(isocyanatomethyl)cyclohexane, 2,2,4-trimethylhexane 1,6-diisocyanate, 2,4,4-trimethylhexane 1,6-diisocyanate, 2,5(6)-bis(isocyanatomethyl)cyclo[2.2.1.] heptane, 1,3,3-trimethyl-1-(isocyanatomethyl)-5-isocyanatocyclohexane, 1,8-diisocyanato-2,4-dimethyloctane, octahydro-4,7-methano-1H-indenedimethyl diisocyanate, and 1,1'-methylenebis(4-isocyanatocyclohexane), and 4,4-methylene dicyclohexyl diisocyanate ($H_{12}$MDI). Examples of aromatic diisocyanates include 1,3-phenylene diisocyanate, 1,4-phenylene diisocyanate, 2,6-toluene diisocyanate (2,6-TDI), 2,4-toluene diisocyanate (2,4-TDI), a blend of 2,4-TDI and 2,6-TDI, 1,5-diisocyanatonaphthalene, diphenyl oxide 4,4'-diisocyanate, 4,4'-methylenediphenyl diisocyanate (4,4-MDI), 2,4'-methylenediphenyl diisocyanate (2,4-MDI), 2,2'-diisocyanatodiphenylmethane (2,2-MDI), diphenylmethane diisocyanate (MDI), 3,3'-dimethyl-4,4'-biphenylene isocyanate, 3,3'-dimethoxy-4,4'-biphenylene diisocyanate, 1-[(2,4-diisocyanatophenyl)methyl]-3-isocyanato-2-methyl benzene, and 2,4,6-triisopropyl-m-phenylene diisocyanate.

Examples of alicyclic diisocyanates from which the diisocyanates may be selected include isophorone diisocyanate (IPDI), cyclohexane diisocyanate, methylcyclohexane diisocyanate, bis(isocyanatomethyl)cyclohexane, bis(isocyanatocyclohexyl)methane, bis(isocyanatocyclohexyl)-2,2-propane, bis(isocyanatocyclohexyl)-1,2-ethane, 2-isocyanatomethyl-3-(3-isocyanatopropyl)-5-isocyanatomethyl-bicyclo[2.2.1]-heptane, 2-isocyanatomethyl-3-(3-isocyanatopropyl)-6-isocyanatomethyl-bicyclo[2.2.1]-heptane, 2-isocyanatomethyl-2-(3-isocyanatopropyl)-5-isocyanatomethyl-bicyclo[2.2.1]-heptane, 2-isocyanatomethyl-2-(3-isocyanatopropyl)-6-isocyanatomethyl-bicyclo[2.2.1]-heptane, 2-isocyanatomethyl-3-(3-isocyanatopropyl)-6-(2-isocyanatoethyl)-bicyclo[2.2.1]-heptane, 2-isocyanatomethyl-2-(3-isocyanatopropyl)-5-(2-isocyanatoethyl)-bicyclo[2.2.1]-heptane, and 2-isocyanatomethyl-2-(3-isocyanatopropyl)-6-(2-isocyanatoethyl)-bicyclo[2.2.1]-heptane.

Examples of aromatic diisocyanates in which the isocyanate groups are not bonded directly to the aromatic ring include, but are not limited to, bis(isocyanatoethyl)benzene, α, α, α',α'-tetramethylxylene diisocyanate, 1,3-bis(1-isocyanato-1-methylethyl)benzene, bis(isocyanatobutyl)benzene, bis(isocyanatomethyl)naphthalene, bis(isocyanatomethyl) diphenyl ether, bis(isocyanatoethyl)phthalate, and 2,5-di(isocyanatomethyl)furan. Aromatic diisocyanates having isocyanate groups bonded directly to the aromatic ring include phenylene diisocyanate, ethylphenylene diisocyanate, isopropylphenylene diisocyanate, dimethylphenylene diisocyanate, diethylphenylene diisocyanate, diisopropylphenylene diisocyanate, naphthalene diisocyanate, methylnaphthalene diisocyanate, biphenyl diisocyanate, 4,4'-diphenylmethane diisocyanate, bis(3-methyl-4-isocyanatophenyl)methane, bis (isocyanatophenyl)ethylene, 3,3'-dimethoxy-biphenyl-4,4'-diisocyanate, diphenylether diisocyanate, bis(isocyanatophenylether)ethyleneglycol, bis(isocyanatophenylether)-1,3-propyleneglycol, benzophenone diisocyanate, carbazole diisocyanate, ethylcarbazole diisocyanate, dichlorocarbazole diisocyanate, 4,4'-diphenylmethane diisocyanate, p-phenylene diisocyanate, 2,4-toluene diisocyanate, and 2,6-toluene diisocyanate.

"Group derived from an ethylenically unsaturated monoisocyanate" refers to a group in which the isocyanate group of a parent ethylenically unsaturated monoisocyanate forms a urethane, thiourethane or urea linkage and the ethylenically unsaturated group is bonded to another moiety or that is not bonded to another moiety. In certain embodiments, a group derived from an ethylenically unsaturated isocyanate refers to a group in which an isocyanate group of a parent ethylenically unsaturated monoisocyanate forms a urethane, thiourethane or urea linkage and the ethylenically unsaturated group is not bonded to another moiety. For example, a group derived from the ethylenically unsaturated monoisocyanate 2-isocyanatoethyl methacrylate can have the structure:

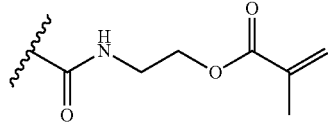 [SMILES: *C(=O)NCCOC(=O)C(=C)C]

where the carbonyl is bonded to —O—, —S—, or —NR— to form a urethane, thiourethane or urea group, respectively. In certain embodiments, a group derived from an ethylenically unsaturated isocyanate refers to a group in which an isocyanate group of a parent ethylenically unsaturated monoisocyanate forms a urethane, thiourethane or urea linkage and the ethylenically unsaturated group is bonded to another moiety. In such embodiments, a group derived from the ethylenically unsaturated monoisocyanate 2-isocyanatoethyl methacrylate has the structure:

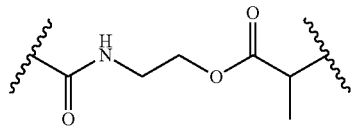 [SMILES: *C(=O)NCCOC(=O)C(*)C]

where the carbonyl is bonded to —O—, —S—, or —NR— to form a urethane, thiourethane or urea group, and the former vinyl group is bonded to another moiety.

"Heteroalkanearene" refers to an alkanearene group in which one or more of the carbon atoms are replaced with a heteroatom, such as N, O, S, or P. In certain embodiments of heteroalkanearene, a heteroatom is selected from N and O.

"Heteroalkanearenediyl" refers to an alkanearenediyl group in which one or more of the carbon atoms are replaced with a heteroatom, such as N, O, S, or P. In certain embodiments of heteroalkanearenediyl, the heteroatom is selected from N and O.

"Heteroalkanecycloalkane" refers to an alkanecycloalkane group in which one or more of the carbon atoms are replaced with a heteroatom, such as N, O, S, or P. In certain embodiments of heteroalkanecycloalkane, the heteroatom is selected from N and O.

"Heteroalkanecycloalkanediyl" refers to an alkanecycloalkanediyl group in which one or more of the carbon atoms are replaced with a heteroatom, such as N, O, S, or P. In certain embodiments of heteroalkanecycloalkanediyl, the heteroatom is selected from N and O.

"Heteroalkanediyl" refers to an alkanediyl group in which one or more of the carbon atoms are replaced with a heteroatom, such as N, O, S, or P. In certain embodiments of heteroalkanediyl, the heteroatom is selected from N and O.

"Heterocycloalkanediyl" refers to a cycloalkanediyl group in which one or more of the carbon atoms are replaced with a heteroatom, such as N, O, S, or P. In certain embodiments of heterocycloalkanediyl, the heteroatom is selected from N and O.

"Heteroalkyl" refers to an alkyl group in which one or more of the carbon atoms are replaced with a heteroatom, such as N, O, S, or P. In certain embodiments of heteroalkyl, the heteroatom is selected from N and O.

"Heteroarenediyl" refers to an arenediyl group in which one or more of the carbon atoms are replaced with a heteroatom, such as N, O, S, or P. In certain embodiments of heteroarenediyl, the heteroatom is selected from N and O.

"Heteroaryl" refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. Heteroaryl encompasses 5- to 7-membered aromatic, monocyclic rings containing one or more, for example, from 1 to 4, or in certain embodiments, from 1 to 3, heteroatoms chosen from N, O, S, and P with the remaining ring atoms being carbon; and bicyclic heterocycloalkyl rings containing one or more, for example, from 1 to 4, or in certain embodiments, from 1 to 3, heteroatoms chosen from N, O, S, and P, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, where the total number of N, O, S, and P atoms in the heteroaryl group exceeds one, the heteroatoms are not adjacent to one another. In certain embodiments, the total number of N, O, S, and P atoms in the heteroaryl group is not more than two. In certain embodiments, the total number of N, O, S, and P atoms in the aromatic heterocycle is not more than one. Heteroaryl does not encompass or overlap with aryl as defined herein. Examples of heteroaryl groups include, but are not limited to, groups derived from acridine, arsindole, carbazole, a-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is $C_{5-20}$heteroaryl, $C_{5-12}$ heteroaryl, $C_{5-10}$ heteroaryl, and in certain embodiments $C_{5-6}$ heteroaryl. In certain embodiments heteroaryl groups are derived from thiophene, pyrrole, benzothiophene, benzofuran, indole, pyridine, quinoline, imidazole, oxazole, or pyrazine.

"Ketone" refers to a compound of the formula $CO(R)_2$ where each R is a hydrocarbon group. In certain embodiments of a ketone, each R is independently selected from $C_{1-6}$ alkyl, $C_{7-12}$ phenylalkyl, substituted $C_{7-12}$ phenylalkyl, $C_{6-12}$ cycloalkylalkyl, and substituted $C_{6-12}$ cycloalkylalkyl. In certain embodiments of the ketone, each R is independently selected from methyl, ethyl, and propyl. In certain embodiments, the ketone is selected from propan-2-one, butan-2-one, pentan-2-one, and pentan-3-one. In certain embodiments of the ketone, each R is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl "Phenylalkyl" refers to an alkyl group in which one of the hydrogen atoms are replaced with a phenyl group. In certain embodiments of phenylalkyl, one of the hydrogen atoms of the terminal carbon atom of an alkyl group is replaced with a phenyl group. In certain embodiments, the phenylalkyl group is $C_{7-12}$ phenylalkyl, $C_{7-10}$ phenylalkyl, $C_{7-9}$ phenylalkyl, and in certain embodiments, benzyl.

"Substituted" refers to a group in which one or more hydrogen atoms are each independently replaced with the same or different substituent(s). In certain embodiments, the substituent is selected from halogen, —$S(O)_2OH$, —$S(O)_2$, —SH, —SR where R is $C_{1-6}$ alkyl, —COOH, —$NO_2$, —$NR_2$ where each R is independently selected from hydrogen and $C_{1-3}$ alkyl, —CN, =O, $C_{1-6}$ alkyl, $C_{1-3}$ alkyl, —$CF_3$, —OH, phenyl, $C_{2-6}$ heteroalkyl, $C_{5-6}$ heteroaryl, $C_{1-6}$ alkoxy, and —COR where R is $C_{1-6}$ alkyl. In certain embodiments, the substituent is chosen from —OH, —$NH_2$, and $C_{1-3}$ alkyl.

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of about 1 and the recited maximum value of about 10, that is, having a minimum value equal to or greater than about 1 and a maximum value of equal to or less than about 10.

Reference is now made to certain embodiments of polymers, compositions, and methods. The disclosed embodiments are not intended to be limiting of the claims. To the contrary, the claims are intended to cover all alternatives, modifications, and equivalents.

Multifunctional Sulfur-Containing Polymers

As indicated, certain embodiments provided by the present disclosure relate to multifunctional sulfur-containing polymers. Sulfur-containing polymers include polythioethers, polydisulfides, and polymers containing both thioether and disulfide groups. Polythioether generally refers to a polymer containing at least two thioether groups, e.g., two —C—S—C— groups. Polydisulfide refers to a polymer containing at least two disulfide groups, e.g., two CSSC groups. In addition to at least two thioether and/or disulfide groups, sulfur-containing polymers provided by the present disclosure comprise at least two formal, acetal, and/or ketal groups, e.g., at least two —O—$CR_2$—O— groups, where each R is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl. As used herein, "polymer" refers to oligomers, homopolymers, and copolymers. Unless stated otherwise, molecular weights are number average molecular weights for polymeric materials indicated as "Mn" as determined, for example, by gel permeation chromatography using a polystyrene standard in an art-recognized manner.

In certain embodiments, sulfur-containing polymers provided by the present disclosure comprise the reaction products of reactants comprising: (a) a sulfur-containing diol; (b) a polyol containing at least three (3) hydroxyl groups per polyol molecule; and (c) a reactant selected from an aldehyde, a ketone, and a combination thereof. The reactants may comprise one or more types of sulfur-containing diol, one or more types of polyol, and/or one or more types of aldehyde and/or ketone.

In certain embodiments of the reaction, the sulfur-containing diol comprises the structure:

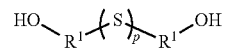

where p is selected from 1 and 2; and each $R^1$ is independently selected from $C_{2-6}$ alkanediyl. In certain embodiments of a sulfur-containing diol, p is 1 and in certain embodiments p is 2. In certain embodiments of a sulfur-containing diol, each $R^1$ is the same and in certain embodiments, each $R^1$ is different. In certain embodiments, each $R^1$ is selected from $C_{2-5}$ alkanediyl, $C_{2-4}$ alkanediyl, $C_{2-3}$ alkanediyl, and in certain embodiments, each $R^1$ is ethane-1,2-diyl. In certain embodiments of the reaction, the sulfur-containing diol comprises a sulfur-containing diol selected from 2,2'-thiodiethanol, 3,3'-thiobis(propan-1-ol), 4,4'-thiobis(butan-1-ol), and a combination of any of the foregoing. In certain embodiments of the reaction, the sulfur-containing diol comprises 2,2'-thiodiethanol.

In certain embodiments of the reaction, the sulfur-containing diol comprises a single type of sulfur-containing diol, and in certain embodiments, comprises a mixture of sulfur-containing diols. A mixture of sulfur-containing diols may comprise from 5 mol % to 95 mol % of one or more thioethers (p is 1) and from 95 mol % to 5 mol % of one or more disulfides (p is 2). In certain embodiments, a mixture of sulfur-containing diols comprises 50 mol % of one or more thioethers and 50 mol % of one or more disulfides. In certain embodiments, a mixture of sulfur-containing diols comprises from 0 mol % to 30 mol % of one or more disulfides, and from 100 mol % to 70 mol % of one or more thioethers.

In certain embodiments, a polyol contains at least three hydroxyl groups per polyol molecule. For example, a polyol may contain from three to ten hydroxyl groups per polyol molecule, from three to eight hydroxyl groups per polyol molecule, from three to six hydroxyl groups per polyol molecule, and in certain embodiments, from three to four hydroxyl groups per polyol molecule. In certain embodiments, a polyol contains four hydroxyl groups per polyol molecule, and in certain embodiments, a polyol contains three hydroxyl groups per polyol molecule. The polyol may be a single type of polyol or may be a mixture of different polyols having the same or different number of hydroxyl groups per molecule.

In certain embodiments, a polyol comprises a triol of Formula (1):

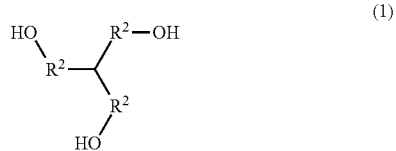

(1)

where each $R^2$ is independently $C_{1-6}$ alkanediyl; and in certain embodiments, a polyol comprises a triol of Formula (2):

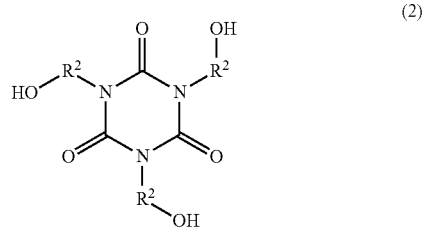

(2)

where each $R^2$ is independently $C_{1-6}$ alkanediyl. In certain embodiments of a polyol of Formula (1) and Formula (2), each $R^2$ may be independently selected from a $C_{1-4}$ alkanediyl, and in certain embodiments from a $C_{1-3}$ alkanediyl. In certain embodiments, each $R^2$ may be the same, and in certain embodiments, each $R^2$ may be different. In certain embodiments of a polyol of Formula (1) and Formula (2), each $R^2$ is selected from methanediyl, ethane-1,2-diyl, propane-1,3-diyl, and in certain embodiments, butane-1,4-diyl.

In certain embodiments of the reaction, reactant (c) is an aldehyde. In certain embodiments in which reactant (c) is an aldehyde, the aldehyde comprises a $C_{1-6}$ aldehyde, a $C_{1-4}$ aldehyde, a $C_{1-3}$ aldehyde, and in certain embodiments, a $C_{1-2}$ aldehyde. In certain embodiments, the aldehyde comprises an alkyl and is selected from acetaldehyde, propionaldehyde, isobutyraldehyde, and butyraldehyde. In certain embodiments, the aldehyde is formaldehyde.

In certain embodiments of the reaction, reactant (c) is a ketone. In certain embodiments in which reactant (c) is a ketone, the ketone has the formula $C(O)R_2$ where each R is independently selected from $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl. In certain embodiments of a ketone, each R is independently selected from methyl, ethyl, and propyl. In certain embodiments, a ketone is selected from propan-2-one, butan-2-one, pentan-2-one, pentan-3-one, and 3-methylbutan-2-one.

In certain embodiments, a sulfur-containing polymer of Formula (I) is the reaction products of reactants comprising 2,2'-thiodiethanol and formaldehyde, and is referred to herein as thiodiglycol polythioether or thiodiglycol polyformal.

In embodiments in which the one or more polyols used to form sulfur-containing polymers provided by the present disclosure have the same number of hydroxyl groups, the sulfur-containing polymer will have a hydroxyl functionality approximately equivalent to that of the polyols. For example, when a polyol having a hydroxyl functionality of three or a mixture of polyols in which each of the polyols in the mixture has a hydroxyl functionality of three is used to prepare a sulfur-containing polymer, the sulfur-containing polymer will have a hydroxyl functionality of three. In certain embodiments, a sulfur-containing polymer may have an average hydroxyl functionality of three, four, five, and in certain embodiments, six.

When polyols having different hydroxyl functionalities are used to prepare multifunctional sulfur-containing polymers, the multifunctional sulfur-containing polymers can exhibit a range of functionalities. For example, multifunctional sulfur-containing polymers provided by the present disclosure may have an average hydroxyl functionality from 3 to 12, from 3 to 9, from 3 to 6, from 3 to 4, and in certain embodiments, from 3.1 to 3.5. In certain embodiments, a sulfur-containing polymer having an average hydroxyl functionality from three to four may be prepared by reacting a combination of one or more polyols having a hydroxyl functionality of three and one or more polyols having a hydroxyl functionality of four.

In certain embodiments, sulfur-containing polymers of Formula (I) have a hydroxyl number from 10 to 100, from 20 to 80, from 20 to 60, from 20 to 50, and in certain embodiments, from 20 to 40. The hydroxyl number is the hydroxyl content of the sulfur-containing polymer, and may be determined, for example, by acetylating the hydroxyl groups and titrating the resultant acid against potassium hydroxide. The hydroxyl number is the weight of potassium hydroxide in milligrams that will neutralize the acid from one gram of the sulfur-containing polymer.

In certain embodiments, a sulfur-containing polymer provided by the present disclosure has a number average molecular weight from 200 to 6,000 Daltons, from 500 to 5,000 Daltons, from 1,000 to 4,000 Daltons, from 1,500 to 3,500 Daltons, and in certain embodiments, from 2,000 Daltons to 3,000 Daltons.

In certain embodiments, a sulfur-containing polymer provided by the present disclosure is the reaction products of reactants comprising 2,2'-thiodiethanol, formaldehyde, and a triol of Formula (1). In certain embodiments, a sulfur-containing polymer provided by the present disclosure is the reaction products of reactants comprising 2,2'-thiodiethanol, formaldehyde, and a triol of Formula (2).

The reaction used to prepare a sulfur-containing polymer of Formula (I) may take place in the presence of an acidic catalyst, such as sulfuric acid, sulfonic acid, or a combination thereof. In certain embodiments, a sulfonic acid may be used. Examples of sulfonic acids include alkyl sulfonic acids such as methane sulfonic acid, ethane sulfonic acid tert-butane sulfonic acid, 2-propane sulfonic acid, and cyclohexyl sulfonic acid; alkene sulfonic acids such as a-olefin sulfonic acid, dimerized a-olefin sulfonic acid, and 2-hexene sulfonic acid; aromatic sulfonic acids such as para-toluene sulfonic acids, benzene sulfonic acid, and naphthalene sulfonic acid; and polymer-supported sulfonic acids such as AMBERLYST™ sulfonic acid catalysts available from Dow Chemical.

In certain embodiments, a multifunctional sulfur-containing polymer has the structure of Formula (I):

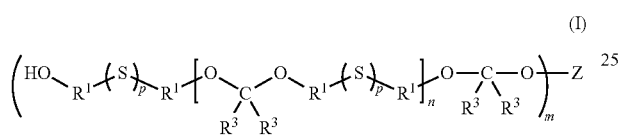

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$. Each $R^1$ may be the same or may be different, and each $R^2$ may be the same or may be different.

In certain embodiments of a sulfur-containing polymer of Formula (I), each $R^1$ is independently selected from $C_{2-6}$ alkanediyl, $C_{2-4}$ alkanediyl, $C_{2-3}$ alkanediyl, and in certain embodiments, ethane-1,2-diyl. In certain embodiments of a compound of Formula (I), each $R^1$ is ethane-1,2-diyl.

In certain embodiments of a sulfur-containing polymer of Formula (I), each $R^3$ is independently selected from hydrogen, $C_{1-6}$ alkyl, $C_{1-4}$ alkyl, $C_{1-3}$ alkyl, and $C_{1-2}$ alkyl. In certain embodiments of a compound of Formula (I), each $R^3$ is methyl, and in certain embodiments, ethyl. In certain embodiments of a compound of Formula (I), each $R^3$ is hydrogen, and in certain embodiments, each $R^3$ is selected from hydrogen, methyl, and ethyl. In certain embodiments of a compound of Formula (I), each $R^1$ is ethane-1,2-diyl and each $R^3$ is hydrogen.

In certain embodiments of a sulfur-containing polymer of Formula (I), each $R^1$ is the same and is selected from $C_{2-3}$ alkanediyl such as ethane-1,2-diyl and propane-1,3-diyl; and each $R^3$ is the same and is selected from hydrogen and $C_{1-3}$ alkyl such as methyl, ethyl, and propyl. In certain embodiments of a sulfur-containing polymer of Formula (I), each $R^3$ is hydrogen, and in certain embodiments, each $R^3$ is methyl. In certain embodiments of a sulfur-containing polymer of Formula (I), each $R^1$ is ethane-1,2-diyl and each $R^3$ is hydrogen. In certain embodiments of a sulfur-containing polymer of Formula (I), each $R^1$ is the same and is selected from ethane-1,2-diyl and propane-1,3-diyl; and each $R^3$ is independently selected from hydrogen, methyl, and ethyl.

In certain embodiments of a sulfur-containing polymer of Formula (I), n is an integer selected from 1 to 50, an integer selected from 2 to 40, an integer selected from 4 to 30, and in certain embodiments, an integer selected from 7 to 30.

In certain embodiments of a sulfur-containing polymer of Formula (I), each p is the same and is 1, and in certain embodiments, each p is the same and is 2.

In certain embodiments of a compound of Formula (I), m is 1, m is 2, m is 3, m is 4, m is 5, and in certain embodiments, m is 6.

In certain embodiments of a compound of Formula (I), m is 3 and the parent polyol $Z(OH)_m$ is a triol of Formula (1):

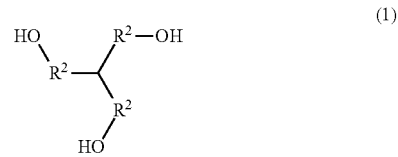

where each $R^2$ is independently $C_{1-6}$ alkanediyl, and in certain embodiments, a triol of Formula (2):

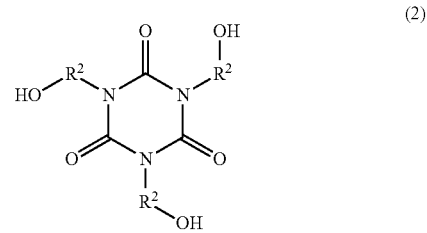

where each $R^2$ is independently $C_{1-6}$ alkanediyl. Accordingly, Z has the structure:

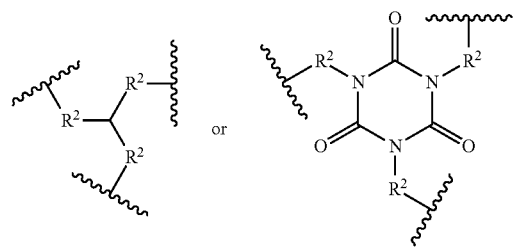

respectively where each $R^2$ is independently a $C_{1-4}$ alkanediyl, and each —— represents a bond to the group within the outer parenthesis of Formula (I).

In certain embodiments, a sulfur-containing polymer of Formula (I) has a hydroxyl number from 10 to 100, from 20 to 80, from 20 to 60, from 20 to 50, and in certain embodiments, from 20 to 40.

In certain embodiments, a sulfur-containing polymer of Formula (I) has a number average molecular weight from 200 to 6,000 Daltons, from 500 to 5,000 Daltons, from 1,000 to 4,000 Daltons, from 1,500 to 3,500 Daltons, and in certain embodiments, from 2,000 Daltons to 3,000 Daltons.

Terminal-Modified Sulfur-Containing Polymers

Hydroxyl-terminated multifunctional sulfur-containing polymers of Formula (I) may be derivatized such that the terminal hydroxyl groups are replaced with a group selected from a vinyl-terminated group, an epoxy-terminated group, an amine-terminated group, a silyl-terminated group, a thiol-terminated group, and an isocyanate terminated group.

In certain embodiments, a terminal-modified sulfur-containing polymer comprises the reaction products of reactants comprising (a) a sulfur-containing polymer of Formula (I):

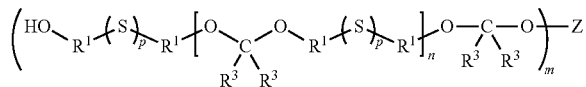
(I)

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (b) a compound comprising a terminal group selected from a vinyl group, a silyl group, an epoxy group, and an isocyanate group; and a group that is reactive with the terminal hydroxyl groups of the polymer of Formula (I).

In certain embodiments, a terminal-modified sulfur-containing polymer comprises the reaction products of reactants comprising (a) a sulfur-containing polymer of Formula (I):

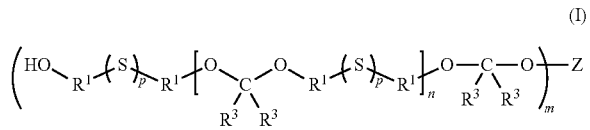
(I)

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (b) a compound comprising a terminal group selected from a vinyl group, a silyl group, and an epoxy group; and a group that is reactive with the terminal hydroxyl groups of the polymer of Formula (I).

In certain embodiments, a terminal-modified sulfur-containing polymer comprises the reaction products of reactants comprising (a) a sulfur-containing polymer of Formula (I):

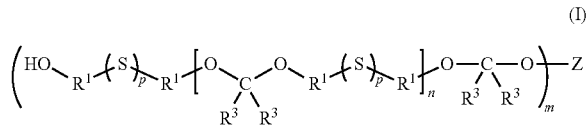
(I)

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (b) a compound comprising a terminal group selected from a vinyl group, a silyl group, and an epoxy group; and a group that is reactive with the terminal hydroxyl groups of the polymer of Formula (I).

In certain embodiments of a terminal-modified sulfur-containing polymer, the terminal group is a vinyl group and the compound comprising a terminal vinyl group is selected from an ethylenically unsaturated monoisocyanate and an ethylenically unsaturated alcohol.

An ethylenically unsaturated monoisocyanate includes ethylenically unsaturated aromatic monoisocyanates and ethylenically unsaturated aliphatic monoisocyanates. Examples of ethylenically unsaturated monoisocyanates include vinyl isocyanate, allyl isocyanate, 3-isocyanato-2-methyl-2-propene, methacryloyl isocyanate, isocyanatoethyl methacrylate, vinyl-benzyl isocyanate, 3-isocyanato-1-butene, 3-isocyanato-3-methyl-1-butene, 4-isocyanato-2-methyl-1-butene, 4-isocyanato-3,3-dimethyl-1-butene, 4-isocyanato-4-methyl-1-pentene, and 5-isocyanato-1-pentene, 2-isocyanatoethyl methacrylate, and dimethyl-meta-isopropenylbenzyl isocyanate (TMI). In certain embodiments, an ethylenically unsaturated monoisocyanate is selected from vinyl isocyanate, allyl isocyanate, and methyacryloyl isocyanate. In certain embodiments, an ethylenically unsaturated aliphatic monoisocyanate is selected from $C_{2-10}$ alkenyl isocyanate, $C_{2-8}$ alkenyl isocyanate, $C_{2-6}$ alkenyl isocyanate, and in certain embodiments, $C_{2-3}$ alkenyl isocyanate.

Examples of ethylenically unsaturated alcohols include, for example, allyl alcohol, 3-buten-1-ol, 3-buten-2-ol, ethylene glycol monovinyl ether, ethylene glycol monoallyl ether, diethylene glycol monoallyl ether, glycerin monoallyl ether, trimethylolethane monoallyl ether, trimethylolpropane monoallyl ether, polyethylene glycol monoallyl ether, polypropylene glycol monoallyl ether, 1-vinylcyclobutanol, 2-vinylcyclobutanol, 3-vinylcyclobutanol, vinylphenol, 2-allyl phenol, 4-allylphenol, 4-allyl-2-methoxyphenol, 4-allyl-2,6-dimethoxyphenol, 4-(2-propenyl)-1,2-benzenediol, and 4-(2,4-dihydroxyphenyl)-3-buten-2-one. In certain embodiments, an ethylenically unsaturated alcohol is selected from allyl alcohol, ethylene glycol monoallyl ether, 2-allylphenol, and 4-allylphenol.

In certain embodiments, the compound comprising a vinyl group is an ethylenically unsaturated monoisocyanate and is selected from 3-isopropenyl-α,α-dimethylbenzyl isocyanate (CAS 2094-99-7) and 2-isocyanatoethyl methacrylate.

In certain embodiments of a reaction to form a terminal-modified sulfur-containing polymer, the terminal group is a silyl group and the compound comprising a terminal silyl group is an isocyanatoalkylalkoxysilane. Examples of suitable isocyanatoalkylalkoxysilanes include, for example, isocyanatopropylmethoxysilane, isocyanatopropylmethyldimethoxysilane, isocyanatopropylmethyldiethoxysilane, isocyanatopropyltriethoxysilane, isocyanatopropyltriisopropoxysilane, isocyanatopropylmethyldiisopropoxysilane, isocyanatoneohexyltrimethoxysilane, isocyanatoneohexyldimethoxysilane, isocyanatoneohexyldiethoxysilane, isocyanatoneohexyltriethoxysilane, isocyanatoneohexyltriisopropoxysilane, isocyanatoneohexyldiisopropoxysilane, isocyanatoisoamyltrimethoxysilane, isocyanatoisoamyldimethoxysilane, isocyanatoisoamylmethylsilane, isocyanatoisoamylmethyldiethoxysilane, isocyanatoisoamyltriethoxysilane, isocyanatoisoamyltriisopropoxysilane, and isocyanatoisoamylmethyldiisopropoxysilane. In certain embodiments, the isocyanatoalkyltrialkoxysilane is 3-isocyanatopropyltrimethoxysilane.

In certain embodiments of a reaction to form a terminal-modified sulfur-containing polymer, the terminal group is an epoxy group and the compound comprising a terminal epoxy group is selected from $C_{1-6}$ epoxy alkanol, $C_{1-6}$ epoxy haloalkane, and a combination thereof. Examples of suitable $C_{1-6}$ alkanol epoxides include oxirane-2-ol, oxirane-2-ylmethanol, and 2-(oxirane-2-yl)thanol. Examples of suitable $C_{1-6}$ epoxy haloalkanes include, for example, 2-(chloromethyl)oxirane and 2-(2-chloroethyl)oxirane.

In certain embodiments, a terminal-modified sulfur-containing polymer comprises the reaction products of reactants comprising (a) and (b), where (a) comprises the reaction products of reactants comprising (i) and (ii), where (i) comprises a sulfur-containing polymer of Formula (I), where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (ii) comprises a first compound selected from a diisocyanate, an ethylenically unsaturated monoisocyanate, and a tosylate; and (b) comprises a second compound comprising a terminal group selected from a vinyl group, a silyl group, and an epoxy group; and a group selected from a group that is reactive with an isocyanate group, a group that is reactive with an ethylenically unsaturated group, and a group that is reactive with a tosylate.

In certain embodiments, an amine-terminated sulfur-containing polymer comprises the reaction products of reactants comprising (a) and (b), where (a) comprises the reaction products of reactants comprising (i) and (ii), where (i) comprises a sulfur-containing polymer of Formula (I):

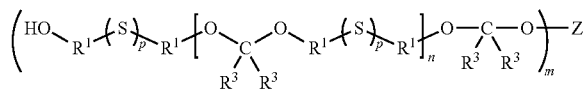

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (ii) comprises a first compound selected from a diisocyanate, an ethylenically unsaturated monoisocyanate, and a tosylate; and (b) comprises a second compound comprising an amine group and a group selected from a group that is reactive with an isocyanate group, an ethylenically unsaturated group, and a tosylate.

In certain embodiments, the first compound is a diisocyanate and is selected from, for example, 1,3-phenylene diisocyanate, 1,4-phenylene diisocyanate, 2,6-toluene diisocyanate (2,6-TDI), 2,4-toluene diisocyanate (2,4-TDI), a blend of 2,4-TDI and 2,6-TDI, 1,5-diisocyanato naphthalene, diphenyl oxide 4,4'-diisocyanate, 4,4'-methylenediphenyl diisocyanate (4,4-MDI), 2,4'-methylenediphenyl diisocyanate (2,4-MDI), 2,2'-diisocyanatodiphenylmethane (2,2-MDI), diphenylmethane diisocyanate (MDI), 3,3'-dimethyl-4,4'-biphenylene isocyanate, 3,3'-dimethoxy-4,4'-biphenylene diisocyanate, 1-[(2,4-diisocyanatophenyl)methyl]-3-isocyanato-2-methyl benzene, 2,4,6-triisopropyl-m-phenylene diisocyanate, 4,4-methylene dicyclohexyl diisocyanate ($H_{12}MDI$), and a combination of any of the foregoing.

In certain embodiments of the reaction to form a terminal-modified sulfur-containing polymer, the first compound is an ethylenically unsaturated monoisocyanate such as 2-isocyanatoethyl methacrylate. Examples of other ethylenically unsaturated monoisocyanates are disclosed herein.

In certain embodiments, the first compound is a tosylate such as a sulfonyl chloride, for example, p-toluenesulfonyl chloride.

In certain embodiments of a reaction to form a terminal-modified sulfur-containing polymer, the second compound comprising a terminal amine group is selected from aniline, an aminoalkyl-substituted aniline, an aminoalkyl, and a sulfur-containing diamine. In certain embodiments, an aminoalkyl-substituted aniline is selected from 4-(aminomethyl)aniline and 4-(aminoethyl)aniline. In certain embodiments an aminoalkyl is selected from ethanamine, propan-1-amine, and butan-1-amine. Suitable sulfur-containing diamines include, for example, ETHACURE® 300.

In certain embodiments of a reaction to form a terminal-modified sulfur-containing polymer, the second compound is an alkyl-aminobenzoate. Examples of suitable alkylaminobenzoates include, for example, methyl 4-aminobenzoate, ethyl 4-aminobenzoate, methyl 3-aminobenzoate, ethyl 3-aminobenzoate, methyl 2-aminobenzoate, and ethyl 3-aminobenzoate. In certain embodiments, an alkyl-aminobenzoate is ethyl 4-aminobenzoate.

In certain embodiments, a thiol-terminated sulfur-containing polymer comprises the reaction products of reactants comprising (a) and (b), where (a) comprises the reaction products of reactants comprising (i) and (ii), where (i) comprises a sulfur-containing polymer of Formula (I):

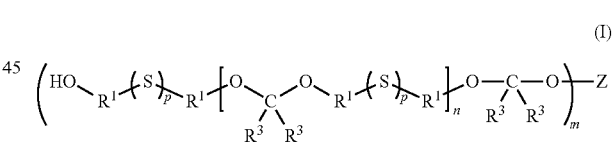

where each n is an integer selected from 1 to 50; m is an integer selected from 3 to 6; each p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and Z represents the core of an m-valent parent polyol $Z(OH)_m$; and (ii) comprises a first compound selected from a diisocyanate, thiourea, an ethylenically unsaturated monoisocyanate, and a tosylate; and (b) comprises a mercaptoalkanol when (ii) comprises a diisocyanate; a metal hydrosulfide when (ii) comprises thiourea; a dithiol when (ii) comprises an ethylenically unsaturated monoisocyanate; and a metal hydrosulfide when (ii) comprises a tosylate.

In certain embodiments, the first compound is a diisocyanates including any of those described herein.

In certain embodiments, the first compound is an ethylenically unsaturated monoisocyanate including any of those described herein.

In certain embodiments, the first compound is tosylate including any of those described herein such as p-toluenesulfonyl chloride.

In certain embodiments, the second compound is a mercaptoalkanol such as, for example, $C_{2-6}$ mercaptoalkanols such as 2-mercaptoethan-1-ol, 3-mercaptopropan-1-ol, 4-mercaptobutan-1-ol, 5-mercaptopentan-1-ol, and 6-mercaptohexan-1-ol. Examples of suitable dithiols include, for example, $C_{2-10}$ alkanedithiols such as ethane-1,2-dithiol, propane-1,3-dithiol, butane-1,4-dithiol, pentane-1,5-dithiol, and hexane-1,6-dithiol.

In certain embodiments, the second compound is a metal hydrosulfide such as sodium hydrosulfide.

In certain embodiments of a reaction to form a terminal-modified sulfur-containing polymer, the compound comprising a terminal thiol group is selected from a dithiol and an alkyl(bis)oxydialkanethiol. In certain embodiments, the second compound is a dithiol including, for example, 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol, dimercaptodiethylsulfide, methyl-substituted dimercaptodiethylsulfide, dimethyl-substituted dimercaptodiethylsulfide, dimethyl-substituted dimercaptodiethylsulfide, dimercaptodioxaoctane, and 1,5-dimercapto-3-oxapentane. A dithiol may have one or more pendant groups selected from $C_{1-4}$ alkyl, $C_{1-4}$ alkoxy, and hydroxyl.

In certain embodiments a dithiol is an alkyl(bis)oxydialkane thiol. Alkyl(bis)oxydialkane thiols may have the general formula HS—R—O—R—O—R—HS, where each R is an alkanediyl such as, for example, $C_{2-6}$ alkanediyl, $C_{2-4}$ alkanediyl, or ethane-1,2-diyl. Suitable dithiols include alkyl (bis)oxyalkanedithiols such as 1,8-dimercapto-3,6-dioxaoctane (DMDO) or dimercaptodiethylsulfide (DMDS). In certain embodiments, a dithiol is selected from dimercaptodiethylsulfide (DMDS), dimercaptodioxaoctane (DMDO), and 1,5-dimercapto-3-oxapentane.

Other examples of suitable dithiols include compounds of the formula HS—R—SH where R is a $C_{2-6}$ alkanediyl, having one or more pendant groups, which can be, for example, hydroxyl groups, $C_{1-6}$ alkyl groups such as methyl or ethyl groups; $C_{1-6}$ alkoxy, $C_{6-8}$ cycloalkanediyl, $C_{6-10}$ alkanecycloalkanediyl, -[—(CH$_2$)$_s$—X—]$_q$—(CH$_2$)$_r$—, or -[—(CH$_2$)$_s$—X—]$_q$—(CH$_2$)$_r$— in which at least one —CH$_2$— unit is substituted with a methyl group and in which each s is independently selected from an integer selected from 2 to 6, each q is independently selected from an integer selected from 1 to 5, and each r is independently selected from an integer selected from 2 to 10. Dithiols may include one or more heteroatom substituents in the carbon backbone, for example, dithiols in which X is a heteroatom such as O, S or other bivalent heteroatom radical, a secondary or tertiary amine group such as —NR—, where R is hydrogen or methyl, or another substituted trivalent heteroatom. In certain embodiments, X is O or S, and in certain embodiments, p and r are equal, and in certain embodiments both p and r are 2. In certain embodiments, X is a bond. Other examples of suitable dithiols are disclosed, for example, in U.S. Pat. No. 6,172,179, which is incorporated by reference in its entirety.

In certain embodiments of the above terminal-modified sulfur-containing polymers, the terminal-modified sulfur-containing polymer has a number average molecular weight from 200 to 6,000 Daltons, from 500 to 5,000 Daltons, from 1,000 to 5,000 Daltons, from 1,500 to 4,000 Daltons, and in certain embodiments, from 2,000 to 3,600 Daltons.

Certain terminal-modified sulfur-containing polymers provided by the present disclosure have the structure of Formula (II):

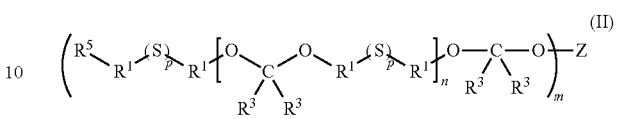

where each n is an integer selected from 1 to 50; m is an integer selected from 3 to 6; p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; each $R^5$ is —OR$^{5'}$ wherein $R^{5'}$ is selected from a vinyl-terminated group, a silyl-terminated group, an amine-terminated group, an epoxy-terminated group, a thiol-terminated group, and an isocyanate-terminated group; and Z represents the core of an m-valent parent polyol Z(OH)$_m$.

Certain terminal-modified sulfur-containing polymers provided by the present disclosure have the structure of Formula (II):

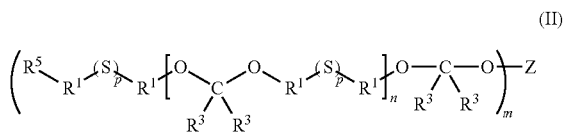

where each n is an integer selected from 1 to 50; m is an integer selected from 3 to 6; p is independently selected from 1 and 2; each $R^1$ is independently selected from $C_{2-6}$ alkanediyl; each $R^3$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; each $R^5$ is —OR$^{5'}$ wherein $R^{5'}$ is selected from a vinyl-terminated group, a silyl-terminated group, an amine-terminated group, an epoxy-terminated group, and a thiol-terminated group; and Z represents the core of an m-valent parent polyol Z(OH)$_m$.

In certain embodiments of a sulfur-containing polymer of Formula (II), each $R^1$ is independently selected from $C_{2-6}$ alkanediyl, $C_{2-4}$ alkanediyl, $C_{2-3}$ alkanediyl, and in certain embodiments, ethane-1,2-diyl. In certain embodiments of a sulfur-containing polymer of Formula (II), each $R^1$ is ethane-1,2-diyl.

In certain embodiments of a sulfur-containing polymer of Formula (II), each $R^3$ is independently selected from hydrogen, $C_{1-6}$ alkyl, $C_{1-4}$ alkyl, $C_{1-3}$ alkyl, and in certain embodiments, $C_{1-2}$ alkyl. In certain embodiments of a sulfur-containing polymer of Formula (II), each $R^3$ is hydrogen, and in certain embodiments, methyl, and in certain embodiments ethyl.

In certain embodiments of a sulfur-containing polymer of Formula (II), each $R^1$ is the same and is selected from a $C_{2-3}$ alkanediyl such as ethane-1,2-diyl and propane-1,3-diyl; and each $R^3$ is the same and is selected from hydrogen and $C_{1-3}$ alkyl such as methyl, ethyl, and propyl. In certain embodiments of a sulfur-containing polymer of Formula (II), each $R^1$ is ethane-1,2-diyl. In certain embodiments of a sulfur-containing polymer of Formula (II), each $R^3$ is hydrogen. In certain embodiments of a sulfur-containing polymer of Formula (II), each $R^1$ is ethane-1,2-diyl and each $R^3$ is hydrogen.

In certain embodiments of a compound of Formula (II), m is 1, m is 2, m is 3, m is 4, m is 5, and in certain embodiments, m is 6.

In certain embodiments of a sulfur-containing polymer of Formula (II) where m is 3, the parent polyol $Z(OH)_m$ is a triol of Formula (1):

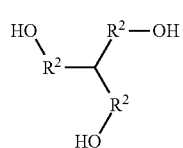

where each $R^2$ is independently $C_{1-6}$ alkanediyl, and in certain embodiments, a triol of Formula (2):

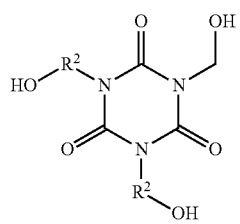

where each $R^2$ is independently $C_{1-6}$ alkanediyl. Accordingly, in these embodiments Z has the structure:

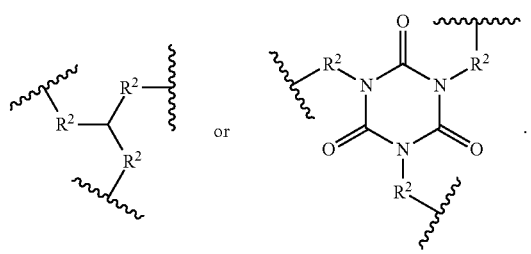

respectively, where each $R^2$ is independently $C_{1-6}$ alkanediyl.

In certain embodiments of a sulfur-containing polymer of Formula (II), each n is an integer selected from 1 to 50, an integer selected from 2 to 40, an integer selected from 4 to 30, and in certain embodiments, an integer selected from 7 to 30.

In certain embodiments of a sulfur-containing polymer of Formula (II), each p is the same and is 1, and in certain embodiments, each p is the same and is 2.

In certain embodiments, a sulfur-containing polymer of Formula (II) has a number average molecular weight from 200 to 6,000 Daltons, from 500 to 5,000 Daltons, from 1,000 to 5,000 Daltons, from 1,500 to 4000 Daltons, and in certain embodiments, from 2,000 to 3,600 Daltons.

In certain embodiments of a sulfur-containing polymer of Formula (II), each $R^5$ is the same.

In certain embodiments of a sulfur-containing polymer of Formula (II), each $R^5$ is selected from a vinyl-terminated group of Formula (a), Formula (b), Formula (c), Formula (d), and Formula (e):

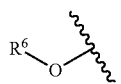

(a)

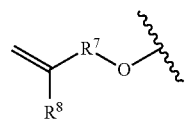

(b)

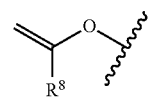

(c)

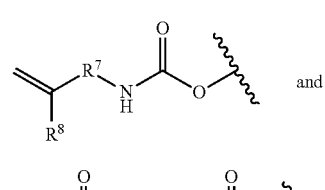

and (d)

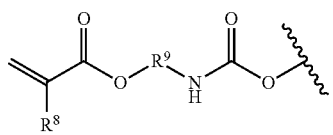

(e)

where each $R^6$ is a moiety derived from an ethylenically unsaturated monoisocyanate; each $R^7$ is selected from $C_{2-6}$ alkanediyl and $C_{2-6}$ heteroalkanediyl; each $R^8$ is selected from hydrogen, $C_{1-6}$ alkyl, and phenyl; and each $R^9$ is selected from $C_{2-6}$ alkanediyl, $C_{2-6}$ heteroalkanediyl, $C_{6-12}$ arenediyl, substituted $C_{6-12}$ arenediyl, $C_{6-12}$ heteroarenediyl, substituted $C_{6-12}$ heteroarenediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{7-18}$ alkanearenediyl, substituted $C_{7-18}$ heteroalkanearenediyl, $C_{4-18}$ alkanecycloalkanediyl, and substituted $C_{4-18}$ alkanecycloalkanediyl.

In certain embodiments, each $R^6$ is derived from an ethylenically unsaturated aliphatic monoisocyanate, an ethylenically unsaturated alicyclic monoisocyanate, and in certain embodiments, an ethylenically unsaturated aromatic monoisocyanate.

In certain embodiments of Formula (b) and Formula (d), each $R^7$ is selected from $C_{2-4}$ alkanediyl, $C_{2-3}$ alkanediyl, and in certain embodiments is selected from ethane-1,2-diyl, propane-1,3-diyl, propane-1,2-diyl, and propane-1,1-diyl. In certain embodiments of Formula (b) and Formula (d), each $R^7$ is selected from ethane-1,2-diyl and propane-1,3-diyl.

In certain embodiments of Formula (b), Formula (c), Formula (d), and Formula (e), each $R^8$ is selected from hydrogen, methyl, ethyl, isopropyl, and n-propyl.

In certain embodiments of Formula (e), each $R^9$ is selected from $C_{2-6}$ alkanediyl, $C_{6-12}$ arenediyl, substituted $C_{6-12}$ arenediyl, $C_{3-12}$ cycloalkanediyl, substituted $C_{3-12}$ cycloalkanediyl, $C_{7-18}$ alkanearenediyl, substituted $C_{7-18}$ alkanearenediyl, $C_{4-18}$ alkanecycloalkanediyl, and substituted $C_{4-18}$ alkanecycloalkanediyl. In certain embodiments of Formula (e), each $R^9$ is the same and is selected from methane-diyl, ethane-1,2-diyl, and propane-1,2-diyl. In certain embodiments of Formula (e), each $R^9$ is $C_{2-5}$ alkanediyl, $C_{2-4}$ alkanediyl, $C_{2-3}$ alkanediyl, and in certain embodiments, ethane-1,2-diyl.

In certain embodiments of sulfur-containing polymers of Formula (II), each $R^5$ is selected from a silyl-terminated group of Formula (f) and Formula (g):

(f)
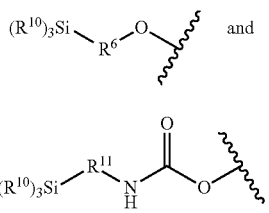

(g)

where each $R^6$ is derived from an ethylenically unsaturated monoisocyanate; each $R^{10}$ is independently selected from $C_{1-6}$ alkyl, $C_{1-6}$ alkoxy, $C_{5-6}$ cycloalkyl, $C_{6-12}$ cycloalkylalkyl, phenyl, and $C_{7-12}$ phenylalkyl; wherein at least one $R^{10}$ is $C_{1-6}$ alkoxy; and each $R^{11}$ is $C_{1-6}$ alkanediyl.

In certain embodiments of Formula (g), each $R^{11}$ is selected from methane-diyl, ethane-1,2-diyl, and propane-1,2-diyl. In certain embodiments of Formula (f) and Formula (g), each $R^{10}$ is the same and is selected from methoxy, ethoxy, and propoxy. In certain embodiments of Formula (f) and Formula (g), the silyl-terminal group is a trialkoxysilane, in certain embodiments, a dialkoxysilane, and in certain embodiments, a monoalkoxysilane.

In certain embodiments of sulfur-containing polymers of Formula (II), each $R^5$ is selected from an amine-terminated group of Formula (h), Formula (i), Formula (j), Formula (k), Formula (l), and Formula (m):

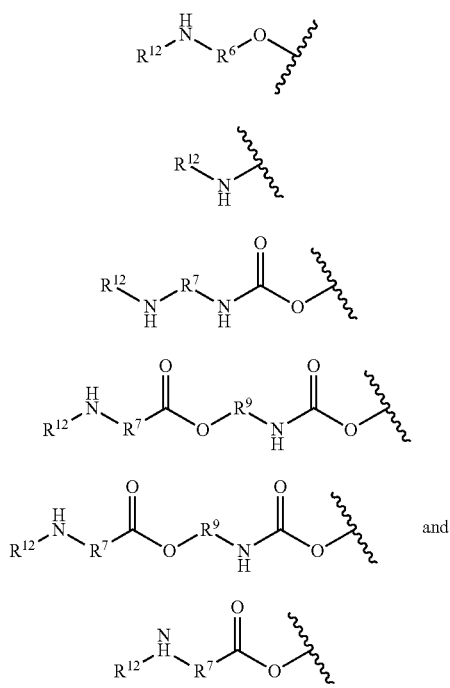

where each $R^6$ is selected from a group derived from a diisocyanate and a group derived from an ethylenically unsaturated monoisocyanate; each $R^7$ is selected from a bond and $C_{2-6}$ alkanediyl; each $R^9$ is selected from $C_{2-6}$ alkanediyl, $C_{2-6}$ heteroalkanediyl, $C_{6-12}$ arenediyl, substituted $C_{6-12}$ arenediyl, $C_{6-12}$ heteroarenediyl, substituted $C_{6-12}$ heteroarenediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{7-18}$ alkanearenediyl, substituted $C_{7-18}$ heteroalkanearenediyl, $C_{4-18}$ alkanecycloalkanediyl, and substituted $C_{4-18}$ alkanecycloalkanediyl; and each $R^{12}$ is selected from hydrogen, $C_{1-6}$ alkyl, $C_{6-12}$ aryl, substituted $C_{6-12}$ aryl, $C_{3-12}$ cycloalkyl, substituted $C_{3-12}$ cycloalkyl, $C_{7-18}$ arylalkyl, substituted $C_{7-18}$ arylalkyl, $C_{4-18}$ alkylcycloalkyl, and substituted $C_{4-18}$ alkylcycloalkyl.

In certain embodiments of Formula (h), each $R^6$ is a group derived from a diisocyanate, and in certain embodiments the group is derived from TDI, ISONATE™ 143L (polycarbodiimide-modified diphenylmethane diisocyanate), DESMODUR® N3400 (1,3-diazetidine-2,4-dione, 1,3-bis(6-isocyanatohexyl)-), DESMODUR® (I) (isophorone diisocyanate, IPDI), of DESMODUR® W ($H_{12}$MDI).

In certain embodiments of Formula (h), each $R^6$ is a group derived from an ethylenically unsaturated monoisocyanate, and in certain embodiments is selected from 2-isocyanatoethyl methacrylate.

In certain embodiments of Formula (j), Formula (k), Formula (l), and Formula (m), each $R^7$ is selected from $C_{2-4}$ alkanediyl, $C_{2-3}$ alkanediyl, and in certain embodiments is selected from ethane-1,2-diyl, propane-1,3-diyl, propane-1,2-diyl, and propane-1,1-diyl. In certain embodiments of Formula (j), Formula (k), Formula (l), and Formula (m), each $R^7$ is selected from ethane-1,2-diyl and propane-1,3-diyl.

In certain embodiments of Formula (k) and Formula (l), each $R^9$ is selected from $C_{2-6}$ alkanediyl, $C_{6-12}$ arenediyl, substituted $C_{6-12}$ arenediyl, $C_{3-12}$ cycloalkanediyl, substituted $C_{3-12}$ cycloalkanediyl, $C_{7-18}$ alkanearenediyl, substituted $C_{7-18}$ alkanearenediyl, $C_{4-18}$ alkanecycloalkanediyl, and substituted $C_{4-18}$ alkanecycloalkanediyl.

In certain embodiments of Formula (h), Formula (i), Formula (j), Formula (k), Formula (l), and Formula (m), each $R^{12}$ is selected from $C_{1-6}$ alkyl, phenyl, and amino-substituted phenyl. In certain embodiments of Formula (h), Formula (i), Formula (j), Formula (k), Formula (l), and Formula (m), each $R^{12}$ is selected from phenyl, methyl, ethyl, propyl, methylphenyl, ethyl-phenyl, propyl-phenyl, benzyl, phenethyl, —($CH_2$)-aniline, and aminophenyl.

In certain embodiments of a sulfur-containing polymer of Formula (II), each $R^5$ is selected from an epoxy-terminated group of Formula (n):

(n)
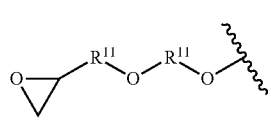

where each $R^{11}$ is independently $C_{1-6}$ alkanediyl.

In certain embodiments of Formula (n), each $R^{11}$ is selected from methanediyl, ethane-1,2-diyl, and propane-1,3-diyl. In certain embodiments, each $R^{11}$ is the same and is selected from methanediyl, ethane-1,2-diyl, and propane-1,3-diyl.

In certain embodiments of a sulfur-containing polymer of Formula (II), each $R^5$ is selected from a thiol-terminated group of Formula (o), Formula (p), Formula (q), Formula (r), Formula (s), Formula (t), Formula (u), and Formula (v):

(o)
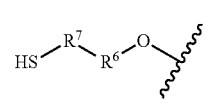

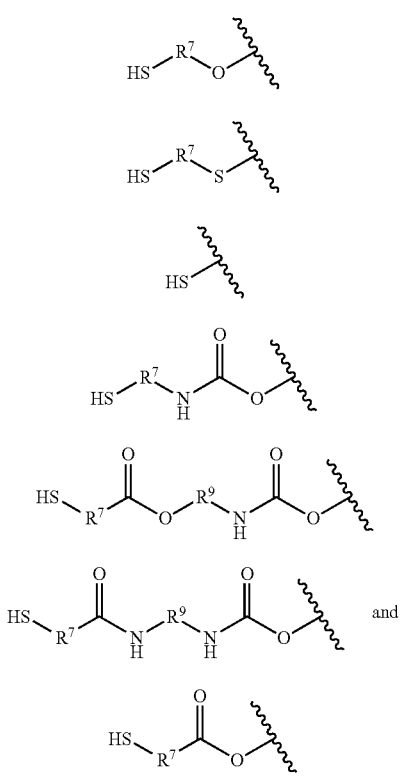

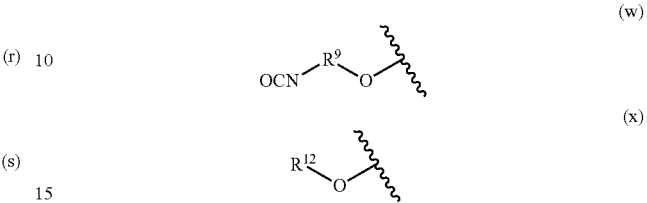

where each R⁶ is selected from a moiety derived from a diisocyanate and a moiety derived from an ethylenically unsaturated monoisocyanate; each $R^7$ is selected from $C_{2-14}$ alkanediyl and $C_{2-14}$ heteroalkanediyl; and each $R^9$ is selected from $C_{2-6}$ alkanediyl, $C_{2-6}$ heteroalkanediyl, $C_{6-12}$ arenediyl, substituted $C_{6-12}$ arenediyl, $C_{6-12}$ heteroarenediyl, substituted $C_{6-12}$ heteroarenediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{7-18}$ alkanearenediyl, substituted $C_{7-18}$ heteroalkanearenediyl, $C_{4-18}$ alkanecycloalkanediyl, and substituted $C_{4-18}$ alkanecycloalkanediyl.

In certain embodiments of Formula (o), each $R^6$ is a group derived from a diisocyanate, and in certain embodiments the group is derived from TDI, ISONATE™ 143L (polycarbodiimide-modified diphenylmethane diisocyanate), DESMODUR® N3400 (1,3-diazetidine-2,4-dione, 1,3-bis(6-isocyanatohexyl)-), DESMODUR® I (isophorone diisocyanate, IPDI), or DESMODUR® W ($H_{12}$MDI).

In certain embodiments of Formula (o), each $R^6$ is a group derived from an ethylenically unsaturated monoisocyanate, and in certain embodiments is 2-isocyanatoethyl methacrylate.

In certain embodiments of Formula (o), Formula (p), Formula (q), Formula (s), Formula (t), Formula (u), and Formula (v), each $R^7$ is selected from $C_{2-6}$ alkanediyl. In certain embodiments of Formula (o), Formula (p), Formula (q), Formula (s), Formula (t), Formula (u), and Formula (v), each $R^7$ is selected from —$CH_2$—S—$(CH_2)_2$—O—$(CH_2)_2$—O—$(CH_2)_2$—, —$(CH_2)_2$—O—$(CH_2)_2$-O—$(CH_2)_2$—, and —$(CH_2)_2$—S—$(CH_2)_2$—O—$(CH_2)_2$—O—$(CH_2)_2$—.

In certain embodiments of Formula (t) and Formula (u), each $R^9$ is selected from $C_{2-6}$ alkanediyl, $C_{6-12}$ arenediyl, substituted $C_{6-12}$ arenediyl, $C_{3-12}$ cycloalkanediyl, substituted $C_{3-12}$ cycloalkanediyl, $C_{7-18}$ alkanearenediyl, substituted $C_{7-18}$ alkanearenediyl, $C_{4-18}$ alkanecycloalkanediyl, and substituted $C_{4-18}$ alkanecycloalkanediyl.

In certain embodiments of a sulfur-containing polymer of Formula (II), each $R^5$ is selected from an isocyanate-terminated group of Formula (w) and Formula (x):

where each $R^9$ is selected from $C_{2-6}$ alkanediyl, $C_{2-6}$ heteroalkanediyl, $C_{6-12}$ arenediyl, substituted $C_{6-12}$ arenediyl, $C_{6-12}$ heteroarenediyl, substituted $C_{6-12}$ heteroarenediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{7-18}$ alkanearenediyl, substituted $C_{7-18}$ heteroalkanearenediyl, $C_{4-18}$ alkanecycloalkanediyl, and substituted $C_{4-18}$ alkanecycloalkanediyl; and each $R^{12}$ is a group derived from a diisocyanate.

In certain embodiments of Formula (w), each $R^9$ is selected from $C_{2-6}$ alkanediyl, $C_{6-12}$ arenediyl, substituted $C_{6-12}$ arenediyl, $C_{3-12}$ cycloalkanediyl, substituted $C_{3-12}$ cycloalkanediyl, $C_{7-18}$ alkanearenediyl, substituted $C_{7-18}$ alkanearenediyl, $C_{4-18}$ alkanecycloalkanediyl, and substituted $C_{4-18}$ alkanecycloalkanediyl.

In certain embodiments of Formula (x), each $R^{12}$ is a group derived from a diisocyanate, and in certain embodiments is derived from TDI, ISONATE™ 143L (polycarbodiimide-modified diphenylmethane diisocyanate), DESMODUR® N3400 (1,3-diazetidine-2,4-dione, 1,3-bis(6-isocyanatohexyl)-), DESMODUR® I (isophorone diisocyanate, IPDI), or DESMODUR® W ($H_{12}$MDI).

Synthesis of Sulfur-Containing Polymers

Multifunctional sulfur-containing polymers provided by the present disclosure and precursors thereof may be prepared by a number of methods known to those skilled in the art, including those described in the examples herein. For example, to obtain multifunctional sulfur-containing polymers of Formula (I), a sulfur-containing diol, a polyol containing at least three hydroxyl groups per polyol molecule, and an aldehyde may be reacted in an organic solvent in the presence of a sulfonic acid such as AMBERLYST™ 15 to provide the corresponding multifunctional sulfur-containing polymer of Formula (I).

Synthesis of Terminal-Modified Multifunctional Sulfur-Containing Polymer Derivatives Terminal-modified multifunctional sulfur-containing polymers provided by the present disclosure and precursors thereof may be prepared by a number of methods known to those skilled in the art, including those described in the Examples herein. For example, to obtain terminal-modified multifunctional sulfur-containing polymers of Formula (II), a multifunctional sulfur-containing polymer of Formula (I) may be reacted with a compound having appropriate terminal groups and a group that is reactive with the terminal hydroxyl group of the polymer of Formula (I).

For example, to obtain a vinyl-terminated sulfur-containing polymer of Formula (II), a sulfur-containing polymer of Formula (I) may be reacted with a compound containing a terminal vinyl group and an isocyanate group, e.g., an ethylenically unsaturated monoisocyanate, such as TMI, 2-isocyanatoethyl, or allyl isocyanate, in the presence of dibutyltin dilaurate and benzyl chloride at 76° C. As a further example, a sulfur-containing polymer of Formula (I) may be reacted with an alkane-ol such as 3-butene-1-ol and an aldehyde such as formaldehyde in the presence of a sulfonic acid (e.g., 4.7 meq/g H+) such as AMBERLYST™ 15 in an organic solvent such as toluene to provide a vinyl-terminated sulfur-containing polymer of Formula (II).

Silyl-terminated sulfur-containing polymers of Formula (II) may be prepared, for example, by reacting a sulfur-containing polymer of Formula (I) with an isocyanatoalkyltrialkoxysilane such as a 3-isocyanatopropyltrimethoxysilane or 3-isocyanatopropylethoxysilane in the presence of dibutyltin dilaurate at a temperature of 76° C. to provide the corresponding silyl-terminated sulfur-containing polymer of Formula (II).

Epoxy-terminated sulfur-containing polymers of Formula (II) may be prepared, for example, by reacting a sulfur-containing polymer of Formula (I) in the presence of a monoepoxide such as epichlorohydrin to provide the corresponding epoxy-terminated sulfur-containing polymer of Formula (II).

Amine-terminated sulfur-containing polymers of Formula (III) may be prepared, for example, by reacting a vinyl-terminated sulfur-containing polymer Formula (II)) with aniline, an amino-substituted aniline such as 4-(aminomethyl)aniline, or an alkylamine such as n-butylamine, optionally in the presence of a catalyst such as 1,8-diazabicyclo[5.4.0]undec-7-ene (DBU), in an organic solvent to provide the corresponding amine-terminated sulfur-containing polymer of Formula (III). Alternatively, amine-terminated sulfur-containing polymers of Formula (III) may be obtained by reacting an isocyanate-terminated sulfur-containing polymer of Formula (II) with a diamine such as 4-(aminomethyl)aniline to provide the corresponding amine-terminated sulfur-containing polymer of Formula (III) Amine-terminated sulfur-containing polymers of Formula (III) may also be obtained by reacting a sulfur-containing polymer of Formula (I) with an amino-substituted benzoate such as ethyl-4-aminobenzoate in the presence of $Bu_2SnO$ or NaOMe at elevated temperature to provide the corresponding amine-terminated sulfur-containing polymer of Formula (III). Amine-terminated sulfur-containing polymers of Formula (III) may also be prepared by reacting a tosyl-ester of a sulfur-containing polymer of Formula (III) with an amine-containing compound such as aniline in an organic solvent at elevated temperature to provide the corresponding amine terminated sulfur-containing polymer of Formula (III).

Thiol-terminated sulfur-containing polymers of Formula (IV) may be prepared by reacting a vinyl-terminated sulfur-containing polymer of Formula (IV) such as the 2-isocyanatoethyl methacrylate adduct or the allyl isocyanate adduct as disclosed herein with a dithiol such as DMDO. Thiol-terminated sulfur-containing polymers of Formula (IV) may also be prepared by reacting a tosyl-ester of a sulfur-containing polymer of Formula (I) with NaSH in the presence of MeN$(Bu)_3{}^+Cl^-$ in water to provide the corresponding thiol-terminated sulfur-containing polymer of Formula (IV). Alternatively, a tosyl-ester of a sulfur-containing polymer of Formula (I) may be reacted with thiourea in the presence of MeN$(Bu)_3{}^+Cl^-$ in water to provide the tosylate salt of the thiourea adduct, which may then be reacted in the presence of base at elevated temperature to provide the corresponding thiol-terminated sulfur-containing polymer of Formula (IV). Alternatively, to obtain thiol-terminated sulfur-containing polymers of Formula (IV), a sulfur-containing polymer of Formula (I) may first be reacted with a diisocyanate such as TDI in the presence of dibutyltin dilaurate at 75° C. to 80° C. to provide the corresponding isocyanate-terminated sulfur-containing polymer of Formula (IV). The isocyanate-terminated sulfur-containing polymer of Formula (IV) may then be reacted with a mercaptoalkanol such as 2-mercaptoethanol or 3-mercaptopropanol to provide the corresponding thiol-terminated sulfur-containing polymer of Formula (IV).

Isocyanate-terminated sulfur-containing polymers of Formula (II) may be prepared, for example, by reacting a sulfur-containing polymer of Formula (I) with a diisocyanate such as TDI, ISONATE™ 143L (polycarbodiimide-modified diphenylmethane diisocyanate), DESMODUR® N3400 (1,3-diazetidine-2,4-dione, 1,3-bis(6-isocyanatohexyl)-), DESMODUR® I (isophorone diisocyanate, IPDI), or DESMODUR® W ($H_{12}MDI$), optionally in the presence of a catalyst such as dibutyltin dilaurate, at a temperature from 70° C. to 80° C. Isocyanate-terminated sulfur-containing polymers may be used as intermediates in the synthesis of other terminal-modified sulfur-containing polymers such as certain amine-terminated and thiol-terminated sulfur-containing polymers provided by the present disclosure.

Properties of Terminal-Modified Multifunctional Sulfur-Containing Polymers

In certain embodiments, terminal-modified multifunctional sulfur-containing polymers provided by the present disclosure are liquid at room temperature. Moreover, in certain embodiments, the sulfur-containing polymers have a viscosity, at 100% solids, of no more than 500 poise, such as 10 to 300 poise or, in some cases, 100 to 200 poise, at a temperature of 25° C. and a pressure of 760 mm Hg determined according to ASTM D-2849 §79-90 using a Brookfield CAP 2000 viscometer. In certain embodiments, the $T_g$ (glass transition temperature) of sulfur-containing polymer provided by the present disclosure is not higher than −40° C., and in certain embodiments, is not higher than −50° C.

Uses

Multifunctional sulfur-containing polymers provided by the present disclosure may be used in compositions, such as sealants, coatings, and/or electrical potting compositions that include one or more of the sulfur-containing polymers provided by the present disclosure. A sealant composition refers to a composition capable of producing a film that has the ability to resist operational conditions, such as moisture and temperature, and at least partially block the transmission of materials, such as water, fuel, and other liquid and gases. In certain embodiments, sealant compositions provided by the present disclosure are useful, e.g., as aerospace sealants and as linings for fuel tanks.

In certain embodiments, a composition comprises a hydroxyl-terminated sulfur-containing polymer of Formula (I) or a sulfur-containing polymer produced by the reaction of (a) a sulfur-containing diol; (b) a polyol containing at least three hydroxyl groups per polyol molecule; and (c) a reactant selected from an aldehyde, a ketone, and a combination thereof; a compound having a group that is reactive with hydroxyl groups; and a curing agent. In certain embodiments, a group that is reactive with hydroxyl groups is selected from an isocyanate, an alcohol, and a thiol.

In certain embodiments, a composition comprises a terminal-modified sulfur-containing polymer of Formula (II) or a terminal-modified sulfur-containing polymer, which is the reaction products of any one of the reactions disclosed herein, and at least one curing agent that is reactive with the terminal-modified sulfur-containing polymer.

In certain embodiments, compositions provided by the present disclosure comprise, in addition to a sulfur-containing polymer of Formula (II), or the reaction products of a reaction as disclosed herein, one or more additional sulfur-containing polymers. A sulfur-containing polymer may be any polymer having at least one sulfur atom in the repeating unit, including polymeric thiols, polythiols, thioethers, sulfur-containing polymers, polyformals, and polysulfides. A "thiol," as used herein, refers to a compound comprising a thiol or mercaptan group, that is, an —SH group, either as the sole functional group or in combination with other functional groups, such as hydroxyl groups, as is the case with, for example, thioglycerols. A polythiol refers to such a compound having more than one —SH group, such as a dithiol or higher functionality polythiol. Such thiol groups are typically terminal and/or pendant such that they have an active hydrogen that is reactive with other functional groups. As used herein, the term "polysulfide" refers to any compound that comprises a sulfur-sulfur linkage (—S—S—). A polythiol may comprise both a terminal and/or pendant sulfur (—SH) and a non-reactive sulfur atom (—S— or —S—S—). Thus, the term polythiol generally encompasses sulfur-containing polymers and polysulfides. Examples of additional sulfur-containing polymers useful in compositions provided by the present disclosure include, for example, those disclosed in U.S. Pat. Nos. 6,172,179, 6,509,418, and 7,009,032.

In certain embodiments, compositions provided by the present disclosure comprise a polythioether having the structure:

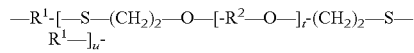

—R¹-[—S—(CH₂)₂—O—[-R²—O—]$_t$-(CH₂)₂—S—R¹—]$_u$-

$R^1$ is selected from a $C_{2-6}$ alkanediyl, $C_{6-8}$ cycloalkanediyl, $C_{6-10}$ cycloalkylalkanediyl, -[(—CH₂—)$_s$—X-]$_q$-(-CH₂—)$_r$-, and -[(—CH₂—)$_s$-X-]$_q$-(-CH₂—)$_r$- in which at least one —CH₂— unit is substituted with a methyl group; $R^2$ is selected from $C_{2-6}$ alkanediyl, $C_{6-8}$ cycloalkanediyl, $C_{6-10}$ cycloalkylalkanediyl, and -[(—CH₂—)$_s$-X-]$_q$-(-CH₂—)$_r$-; X is selected from O, S, and —NR—, where R is selected from hydrogen and methyl; t is an integer selected from 0 to 10; u is an integer selected from 1 to 60; s is an integer selected from 2 to 6; q is an integer selected from 1 to 5, and r is an integer selected from 2 to 10. Such polythioethers are described in U.S. Pat. No. 6,172,179, which is incorporated by reference in its entirety. The one or more additional sulfur-containing polymers may be difunctional or multifunctional, for example, having from 3 to 6 terminal groups, or a mixture thereof.

In certain embodiments, compositions provided by the present disclosure comprise from 10 wt % to 90 wt % of a sulfur-containing polymer provided by the present disclosure, from 20 wt % to 80 wt %, from 30 wt % to 70 wt %, and in certain embodiments from 40 wt % to 60 wt %, where wt % is based on the total weight of all non-volatile components of the composition (i.e., the dry weight). In certain embodiments, compositions provided by the present disclosure comprise from 10 wt % to 90 wt % of a sulfur-containing polymer provided by the present disclosure, from 20 wt % to 90 wt %, from 30 wt % to 90 wt %, from 40 wt % to 90 wt %, from 50 wt % to 90 wt %, from 60 wt % to 90 wt %, from 70 wt % to 90 wt %, and in certain embodiments from 80 wt % to 90 wt %, where wt % is based on the total weight of all non-volatile components of the composition (i.e., the dry weight).

Curing agents suitable in compositions provided by the present disclosure include compounds that are reactive with the terminal groups of the sulfur-containing polymer of Formula (II) or as provided by the reactions disclosed herein, such as compounds that are reactive with hydroxyl groups, vinyl groups, epoxy groups, thiol groups amine groups, or isocyanate groups.

Examples of suitable curing agents that are reactive with hydroxyl groups include diisocyanates and polyisocyanates, examples of which are disclosed herein.

Examples of suitable curing agents that are reactive with vinyl groups include dithiols and polythiols, examples of which are disclosed herein.

Silyl-terminated sulfur-containing polymers provided by the present disclosure hydrolyze in the presence of water inducing self polymerization via condensation. It can be appreciated that because the curing agent for silyl-terminated sulfur-containing polymers may be atmospheric moisture, it is not necessary to include a curing agent to a curable composition containing silyl-terminated sulfur-containing polymers. Therefore, compositions comprising silyl-terminated sulfur-containing polymers and a curing agent for the silyl group refer to atmospheric moisture. Compositions comprising silyl-terminated sulfur-containing polymers may further comprise a catalyst. Catalysts for use with silyl-terminated sulfur-containing polymers include organotitanium compounds such as tetraisopropoxy titanium, tetra-tert-butoxy titanium, titanium di(isopropoxy)bis(ethylacetoacetate), and titanium di(isopropoxy)bis(acetylacetoacetate); organic tin compounds dibutyltin dilaurate, dibutyltin bisacetylacetoacetate, and tin octylate; metal dicarboxylates such as lead dioctylate; organozirconium compounds such as zirconium tetraacetyl acetonate; and organoaluminium compounds such as aluminum triacetyl-acetonate. Specific examples include diisopropoxy bis(ethyl acetoacetate)titanium, diisopropoxy bis(acetyl acetonate)titanium, and dibutoxy bis(methyl acetoacetonate)titanium.

Examples of suitable curing agents that are reactive with epoxy groups include amines such as diethylenetriamine (DTA), triethylenetetramine (TTA), tetraethylenepentamine (TEPA), dipropenediamine (DPDA), diethylaminopropylamine (DEAPA), N-aminoethylpiperazine (N-AEP), isophoronediamine (IPDA), m-xylenediamine, diaminodiphenylmethane (DDM), and diaminodiphenylsulfone (DDS); aromatic amines;ketimine; polyamines; polyamides; phenolic resins; anhydrides such phthalic anhydride, trimellitic anhydride, pyromellitic anhydride, benzophenone tetracarboxylic anhydride, ethylene glycol bistrimellitate, glycerol tristrimellitate, maleic anhydride, tetrahydrophthalic anhydride, methyltetrahydrophthalic anhydride, endomethylene tetrahydrophthalic anhydride; polymercaptans; polysulfides; ultraviolet curing agents such as diphenyliodinium hexafluorophosphate, triphenylsulfonium hexafluorophosphate; and other curing agents known to those skilled in the art.

Examples of suitable curing agents that are reactive with thiol groups include diepoxides.

Examples of suitable curing agents that are reactive with amine groups include isocyanates, diisocyanates, and polymeric polyisocyanates, non-limiting examples of which include polyisocyanates having backbone linkages selected from urethane linkages (—NH—C(O)—O—), thiourethane linkages (—NH—C(O)—S—), thiocarbamate linkages (—NH—C(S)—O—), dithiourethane linkages (—NH—C(S)—S—), and combinations of any of the foregoing.

Examples of suitable curing agents that are reactive with isocyanate groups include diamines, polyamines, polythiols, and polyols, including those disclosed herein.

Compositions provided by the present disclosure may contain from 90% to 150%, from 95% to 125%, and in certain embodiments, from 95% to 105% of the stoichiometric amount, where the stoichiometric amount is the proportion of the number reactive isocyanate groups to the number of groups reactive with the isocyanate groups. For example, a composition containing the same number of isocyanate groups and amine groups prior to reaction will have a stoichiometric amount of isocyanate groups and amine groups.

Compositions provided by the present disclosure may contain one or more different types of filler. Suitable fillers include those commonly known in the art, including inorganic fillers, such as carbon black and calcium carbonate ($CaCO_3$), and lightweight fillers. Suitable lightweight fillers include, for example, those described in U.S. Pat. No. 6,525,168. In certain embodiments, a composition includes 5 wt % to 60 wt % of the filler or combination of fillers, 10 wt % to 50 wt %, and in certain embodiments, from 20 wt % to 40 wt %, based on the total dry weight of the composition.

As can be appreciated, the sulfur-containing polymers, curing agents, and fillers employed in a composition, as well as any additives, may be selected so as to be compatible with each other.

Compositions provided by the present disclosure may include one or more colorants, thixotropic agents, accelerators, retardants, adhesion promoters, solvents, masking agents, or a combination of any of the foregoing.

As used herein, the term "colorant" means any substance that imparts color and/or other opacity and/or other visual effect to the composition. A colorant can be of any suitable form, such as discrete particles, dispersions, solutions, and/or flakes. A single colorant or a mixture of two or more colorants can be used in a composition.

Examples of colorants include pigments, dyes and tints, such as those used in the paint industry and/or listed in the Dry Color Manufacturers Association (DCMA), as well as special effect compositions. A colorant may include, for example, a finely divided solid powder that is insoluble but wettable under the conditions of use. A colorant may be organic or inorganic and may be agglomerated or non-agglomerated. Colorants may be incorporated into a composition by use of a grind vehicle, such as an acrylic grind vehicle.

Examples of pigments and/or pigment compositions include carbazole dioxazine crude pigment, azo, monoazo, diazo, naphthol AS, salt type (flakes), benzimidazolone, isoindolinone, isoindoline, polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red (DPPBO red), titanium dioxide, carbon black, and combinations of any of the foregoing.

Examples of dyes include, but are not limited to, those that are solvent- and/or aqueous-based such as phthalo green or blue, iron oxide, bismuth vanadate, anthraquinone, perylene, and quinacridone.

Examples of tints include pigments dispersed in water-based or water-miscible carriers such as AQUA-CHEM 896 commercially available from Degussa, Inc., CHARISMA COLORANTS and MAXITONER INDUSTRIAL COLORANTS commercially available from Accurate Dispersions division of Eastman Chemical, Inc.

As noted above, a colorant may be in the form of a dispersion including, for example, a nanoparticle dispersion. Nanoparticle dispersions may include one or more highly dispersed nanoparticle colorants and/or colorant particles that produce a desired visible color and/or opacity and/or visual effect. Nanoparticle dispersions may include colorants such as pigments or dyes having a particle size of less than 150 nm, such as less than 70 nm, or less than 30 nm Nanoparticles may be produced by milling stock organic or inorganic pigments with grinding media having a particle size of less than 0.5 mm Examples of nanoparticle dispersions and methods for making them are disclosed in U.S. Pat. No. 6,875,800. Nanoparticle dispersions may also be produced by crystallization, precipitation, gas phase condensation, and/or chemical attrition (i.e., partial dissolution). To minimize re-agglomeration of nanoparticles within the coating, a dispersion of resin-coated nanoparticles may be used. As used herein, a "dispersion of resin-coated nanoparticles" refers to a continuous phase in which are dispersed discreet "composite microparticles" that comprise a nanoparticle and a resin coating on the nanoparticle. Examples of dispersions containing resin-coated nanoparticles and methods for making them are disclosed in U.S. Pat. No. 7,438,972.

Examples of special effect compositions that may be used in compositions provided by the present disclosure include pigments and/or compositions that produce one or more appearance effects such as reflectance, pearlescence, metallic sheen, phosphorescence, fluorescence, photochromism, photosensitivity, thermochromism, goniochromism, and/or color-change. Additional special effect compositions can provide other perceivable properties, such as opacity or texture. In certain embodiments, special effect compositions may produce a color shift, such that the color of a composition changes when the coating is viewed at different angles. Examples of color effect compositions are disclosed in U.S. Pat. No. 6,894,086. Additional color effect compositions may include transparent coated mica and/or synthetic mica, coated silica, coated alumina, a transparent liquid crystal pigment, a liquid crystal coating, and/or any composition wherein interference results from a refractive index differential within the material and not because of the refractive index differential between the surface of the material and the air.

In general, a colorant may comprise from 1 wt % to 65 wt % of a composition, from 2 wt % to 50 wt %, such as from 3 wt % to 40 wt %, or from 5 wt % to 35 wt %, with weight percent based on the total dry weight of the composition.

Thixotropes, for example, silica, may be used in an amount from 0.1 wt % to 5 wt %, based on the total dry weight of the composition.

Cure catalysts known to the art, such as amines, may be present in an amount from 0.1 to 5 weight percent, based on the total weight of the composition. Examples of suitable catalysts include 1,4-diaza-bicyclo[2.2.2]octane (DABCO®, commercially available from Air Products, Chemical Additives Division) and DMP-30® (an accelerant composition including 2,4,6-tris(dimethylaminomethyl)phenol.

Retardants, such as stearic acid, may be used in an amount from 0.1 wt % to 5 wt % of a composition, based on the total dry weight of the composition. Adhesion promoters, may be present in amount from 0.1 wt % to 15 wt % of a composition, based on the total dry weight of the composition. Examples of adhesion promoters include phenolics, such as METHYLON phenolic resin available from Occidental Chemicals, and organosilanes, such as epoxy, mercapto or amino functional silanes, such as SILQUEST® A-187 and SILQUEST® A-1100 available from Momentive Performance Materials. Masking agents, such as pine fragrance or other scents, which may be useful in masking any low level odor of the composition, may be present in an amount from 0.1 wt % to 1 wt %, based on the total dry weight of the composition.

In certain embodiments, compositions provided by the present disclosure may comprise a plasticizer that may facilitate the use of sulfur-containing polymers having a higher glass transition temperature, $T_g$, than would ordinarily be useful in an aerospace sealant. For example, use of a plasticizer may effectively reduce the $T_g$ of a composition, and thereby increase the low-temperature flexibility of the cured polymerizable composition beyond that which would be expected on the basis of the $T_g$ of the sulfur-containing polymers alone. Plasticizers suitable in certain embodiments of the compositions include, for example, phthalate esters, chlorinated paraffins, and hydrogenated terphenyls. A plasticizer or combination of plasticizers may constitute from 1 wt % to 40 wt % of a composition, or from 1 wt % to 10 wt % of a composition. In certain embodiments, a composition may comprise one or more organic solvents, such as isopropyl alcohol, in an amount, for example, from 0 wt % to 15 wt %, from 0 wt % to 10 wt %, or from 0 wt % to 5 wt %, based on the non-dry weight of the composition.

In certain embodiments, compositions provided by the present disclosure are substantially free or, in some cases, completely free, of any solvent, such as an organic solvent or an aqueous solvent, i.e., water. Stated differently, in certain embodiments, compositions provided by the present disclosure are substantially 100% solids.

In certain embodiments, compositions, such as sealant compositions, may be provided as multi-pack compositions, such as two-pack compositions, wherein one package comprises one or more sulfur-containing polymers provided by the present disclosure and a second package comprises one or more curing agents for the one or more sulfur-containing polymers. Additives and/or other materials may be added to either package as desired or necessary. The two packages may be combined and mixed prior to use. In certain embodiments, the pot life of the mixed sulfur-containing polymer and curing agent is at least 30 minutes, at least 1 hour, at least 2 hours, and in certain embodiments, more than 2 hours, where pot life refers to the period of time the composition remains suitable for use as a sealant after mixing.

Compositions provided by the present disclosure may be applied to any of a variety of substrates. Examples of substrates to which a composition may be applied include titanium, stainless steel, and aluminum, which may be anodized, primed, organic-coated or chromate-coated; epoxy; urethane; graphite; fiberglass composite; KEVLAR; acrylics; and polycarbonates.

Compositions provided by the present disclosure may be applied directly onto the surface of a substrate or over an underlayer by any suitable coating process known to those of ordinary skill in the art.

In certain embodiments, compositions provided by the present disclosure are fuel-resistant. As used herein, the term "fuel resistant" means that a composition, when applied to a substrate and cured, can provide a cured product, such as a sealant, that has a percent volume swell of not greater than 40%, in some cases not greater than 25%, in some cases not greater than 20%, in yet other cases not more than 10%, after immersion for one week at 140° F. (60° C.) and ambient pressure in Jet Reference Fluid (JRF) Type I according to methods similar to those described in ASTM D792 (American Society for Testing and Materials) or AMS 3269 (Aerospace Material Specification, Jet Reference Fluid JRF Type I, as employed for determination of fuel resistance, has the following composition (see AMS 2629, issued Jul. 1, 1989, §3.1.1 etc., available from SAE (Society of Automotive Engineers)): toluene: 28±1% by volume; cyclohexane (technical): 34±1% by volume; isooctane: 38±1% by volume; and tertiary dibutyl disulfide: 1±0.005% by volume.

In certain embodiments, compositions provide a cured product, such as a sealant, exhibiting a tensile strength of at least 400 psi and an elongation of at least 100% when measured in accordance with the procedure described in AMS 3279, §3.3.17.1, test procedure AS5127/1, §7.7.

In certain embodiments, compositions provide a cured product, such as a sealant, exhibiting a lap shear strength of greater than 200 psi and in some cases at least 400 psi when measured according to the procedure described in SAE AS5127/1 paragraph 7.8.

In certain embodiments, a cured sealant comprising a sulfur-containing polymer provided by the present disclosure meets or exceeds the requirements for aerospace sealants as set forth in AMS 3277.

Furthermore, methods are provided for sealing an aperture utilizing a composition provided by the present disclosure. These methods comprise, for example, applying a composition provided by the present disclosure to a surface to seal an aperture; and curing the composition. In certain embodiments, a composition may be cured under ambient conditions, where ambient conditions refers to a temperature from 20° C. to 25° C., and atmospheric humidity. In certain embodiments, a composition may be cured under conditions encompassing a temperature from 0° C. to 100° C. and humidity from 0% RH to 100% RH. In certain embodiments, a composition may be cured at a higher temperature such as at least 30° C., at least 40° C., and in certain embodiments, at least 50° C. In certain embodiments, a composition may be cured at room temperature, e.g., 25° C. In certain embodiments, a composition may be cured upon exposure to actinic radiation such as ultraviolet radiation. As will also be appreciated, the methods may be used to seal apertures on aerospace vehicles.

EXAMPLES

Embodiments provided by the present disclosure are further illustrated by reference to the following examples, which describe the synthesis, properties, and uses of certain sulfur-containing polymers. It will be apparent to those skilled in the art that many modifications, both to materials, and methods, may be practiced without departing from the scope of the disclosure.

Example 1

Synthesis of Trifunctional Sulfur-Containing Polymer

Thiodiglycol (1,215.81 g), paraformaldehyde (95% purity) (300.63 g), AMBERLYST™ 15 (212.80 g, Dow Chemical Company), 1,3,5-tris(2-hydroxyethyl) isocyanurate (13.14 g, Aldrich), and toluene (500 mL) were charged in a 3-liter, 4-neck round-bottom flask. The flask was equipped with a heating mantle, thermocouple, temperature controller, and a Dean-Stark adapter fitted with a reflux condenser, a dropping funnel and an inlet for nitrogen positive pressure. During this period, collected water was periodically removed from the Dean-Stark adapter. Stirring was started under nitrogen and the batch was heated to 120° C. and maintained at 120° C. for about 10 hours. The reaction mixture was then cooled to room temperature and filtered with suction through a coarse-fritted Buchner funnel (600 mL volume) with a 9.0 cm-diameter Whatman GF/A filter paper over the frit. The flask and filter cake were washed with 500 mL toluene. A filtrate was obtained. The filtrate was then stripped in vacuo using a 2-L round bottomed flask (rotary evaporator, 5 torr final vacuum, 90° C. water bath). A yellow, viscous polymer (993.53 g) was obtained. The resulting polyformal polymer had a hydroxyl number of 25.3 and a viscosity of 214 poise.

Example 2

Synthesis of Trifunctional Sulfur-Containing Polymer

Thiodiglycol (1,209.67 g), paraformaldehyde (95% purity) (300.48 g), AMBERLYST™ 15 (26.18 g, Dow Chemical Company), 1,3,5-tris(2-hydroxyethyl) isocyanurate (20.9 g, Aldrich), and toluene (500 mL) were charged in a 3-liter, 4-neck round-bottom flask. The flask was equipped with a heating mantle, thermocouple, temperature controller, and a Dean-Stark adapter fitted with a reflux condenser, a dropping funnel and an inlet for nitrogen positive pressure. During this period, collected water was periodically removed from the Dean-Stark adapter. Stirring was started under nitrogen and the batch was heated to 120° C. and maintained at 120° C. for about 10 hours. The reaction mixture was then cooled to room temperature and filtered with suction through a coarse-fritted Buchner funnel (600 mL volume) with a 9.0 cm diameter Whatman GF/A filter paper over the frit. The flask and filter cake were washed with 500 mL toluene. A filtrate was obtained. The filtrate was then stripped in vacuo using a 2-L round bottomed flask (rotary evaporator, 5 torr final vacuum, 90° C. water bath). A yellow, viscous polymer (953.33 g) was obtained. The resulting polyformal polymer had a hydroxyl number of 22.8 and a viscosity of 377 poise.

Example 3

Synthesis of Trifunctional Sulfur-Containing Polymer

Thiodiglycol (1,197.45 g), paraformaldehyde (95% purity) (300.83 g), AMBERLYST™ 15 (213.06 g, Dow Chemical Company), 1,3,5-tris(2-hydroxyethyl) isocyanurate (52.58 g, Aldrich) and toluene (500 mL) were charged in a 3-liter, 4-neck round-bottom flask. The flask was equipped with a heating mantle, thermocouple, temperature controller, and a Dean-Stark adapter fitted with a reflux condenser, a dropping funnel and an inlet for nitrogen positive pressure. During this period, collected water was periodically removed from the Dean-Stark adapter. Stirring was started under nitrogen and the batch was heated to 120° C. and maintained at 120° C. for about 10 hours. The reaction mixture was then cooled to room temperature and filtered with suction through a coarse-fritted Buchner funnel (600 mL volume) with a 9.0 cm-diameter Whatman GF/A filter paper over the frit. The flask and filter cake were washed with 500 mL toluene. A filtrate was obtained. The filtrate was then stripped in vacuo using a 2-L round bottomed flask (rotary evaporator, 5 torr final vacuum, 90° C. water bath). A yellow, viscous polymer (1,039.64 g) was obtained. The resulting polyformal polymer had a hydroxyl number of 23.2 and a viscosity of 942 poise.

Example 4

Acrylate-Terminated Sulfur-Containing Polymer

The sulfur-containing polymer of Example 1 (222.40 g) was charged into a 500-mL, 4-neck round-bottom flask. The flask was equipped with a mantle, thermocouple, temperature controller, an inlet for nitrogen positive pressure, and a mechanical stirrer (PTFE paddle and bearing). The polymer was stirred at ca. 200 rpm and heated to 76.6° C. (170° F.), followed by the addition of isocyanatoethyl methacrylate (15.68 g) and a 0.05% solution of dibutyltin dilaurate dissolved in methyl ethyl ketone (2.51 g). The reaction mixture was maintained at 76.6° C. for 5 h and then cooled to room temperature. The resulting acrylate-terminated polymer (222.08 g) had a viscosity of 299 poise.

Example 5

Acrylate-Terminated Sulfur-Containing Polymer

The sulfur-containing polymer of Example 2 (247.26 g) was charged into a 500-mL, 4-neck round-bottom flask. The flask was equipped with a mantle, thermocouple, temperature controller, an inlet for nitrogen positive pressure, and a mechanical stirrer (PTFE paddle and bearing). The polymer was stirred at ca. 200 rpm and heated to 76.6° C. (170° F.), followed by the addition of isocyanatoethyl methacrylate (15.61 g) and a 0.05% solution of dibutyltin dilaurate dissolved in methyl ethyl ketone (2.66 g). The reaction mixture was maintained at 76.6° C. for 5 h and then cooled to room temperature. The resulting acrylate-terminated polymer (242.14 g) had a viscosity of 439 poise.

Example 6

Acrylate-Terminated Sulfur-Containing Polymer

The sulfur-containing polymer of Example 3 (243.71 g) was charged into a 500-mL, 4-neck round-bottom flask. The flask was equipped with a mantle, thermocouple, temperature controller, an inlet for nitrogen positive pressure, and a mechanical stirrer (PTFE paddle and bearing). The polymer was stirred at ca. 200 rpm and heated to 76.6° C. (170° F.), followed by the addition of isocyanatoethyl methacrylate (15.58 g) and a 0.05% solution of dibutyltin dilaurate dissolved in methyl ethyl ketone (2.74 g). The reaction mixture was maintained at 76.6° C. for 5 h and then cooled to room temperature. The resulting acrylate-terminated polymer (226.09 g) had a viscosity of 1,026 poise.

Example 7

TMI-Terminated Sulfur-Containing Polymer

The sulfur-containing polymer in Example 1 (222.6 g) was charged into a 500-mL, 4-neck round-bottom flask. The flask was equipped with a mantle, thermocouple, temperature controller, an inlet for nitrogen positive pressure, and a mechanical stirrer (PTFE paddle and bearing). The polymer was stirred at ca. 200 rpm and heated to 76.6° C. (170° F.), followed by the addition of 3-isopropenyl-α, α-dimethylbenzyl isocyanate (TMI) (20.25 g, Cytec Industries) and a 0.05% solution of dibutyltin dilaurate dissolved in methyl ethyl ketone (2.47 g). The reaction mixture was maintained at 76.6° C. for 6 hours and then cooled to room temperature. The resulting TMI-terminated polymer (217.32) had a viscosity of 378 poise.

Example 8

TMI-Terminated Sulfur-Containing Polymer

The sulfur-containing polymer in Example 3 (243.70 g) was charged into a 500-mL, 4-neck round-bottom flask. The flask was equipped with a mantle, thermocouple, temperature controller, an inlet for nitrogen positive pressure, and a mechanical stirrer (PTFE paddle and bearing). The polymer was stirred at ca. 200 rpm and heated to 76.6° C. (170° F.), followed by the addition of 3-isopropenyl-$\alpha$,$\alpha$-dimethylbenzyl isocyanate (20.18 g, Cytec Industries) and a 0.05% solution of dibutyltin dilaurate dissolved in methyl ethyl ketone (2.62 g). The reaction mixture was maintained at 76.6° C. for 6 hours and then cooled to room temperature. The resulting TMI-terminated polymer (230.42 g) had a viscosity of 1.261 poise.

Example 9

Curing of Acrylate-Terminated Sulfur-Containing Polymer

The curing reaction was carried out in a 100-g plastic container equipped with a lid. The acrylate-terminated sulfur-containing polymer of Example 4 (40.8 g) and IRGACURE® 2022 (0.2 g, 0.5% by weight) were mixed by hand in the container. The container was then placed in a speed mixer (DAC 600 FVZ) and mixed for 1 min at 2,300 rpm. The polymer was poured over a circular (5 in-diameter) metal lid (pre-treated with Valspar Mold Release 225), and placed under ultraviolet (UV) radiation for 30 sec, after which time the polymer had completely cured. A Super Six curing unit (Fusion Systems Inc.) was used to provide the UV radiation. The curing unit was equipped with a 300 W H-bulb, which produced UV wavelengths ranging from 200 nm to 450 nm A total dosage of 3.103 J/cm$^2$ UV energy, measured using a UV power puck (EIT, Inc., Sterling, Va.) was applied to the polymer composition. A ½ inch-thick disc of cured polymer was obtained. The hardness of the polymer was measured with a durometer to be 53 Shore A. Hardness was determined according to ASTM D 2240.

Example 10

Curing of Acrylate-Terminated Sulfur-Containing Polymer

The curing reaction was carried out in a 100-g plastic container equipped with a lid. The acrylate-terminated sulfur-containing polymer of Example 5 (40.8 g) and IRGACURE® 2022 (0.2 g, 0.5% by weight) were mixed by hand in the container. The container was then placed in a speed mixer (DAC 600 FVZ) and mixed for 1 min at 2,300 rpm. The polymer was poured over a circular (5 in-diameter) metal lid (pre-treated with Valspar Mold Release 225), and placed under ultraviolet (UV) radiation for 30 sec, after which time the polymer had completely cured. A Super Six curing unit (Fusion Systems Inc.) was used to provide the UV radiation. The curing unit was equipped with a 300 W H-bulb, which produced UV wavelengths ranging from 200 nm to 450 nm A total dosage of 3.103 J/cm$^2$ UV energy, measured using a UV power puck (EIT, Inc., Sterling, Va.) was applied to the polymer composition. A ½ inch of cured polymer was obtained. The hardness of the polymer was measured with a durometer to be 51 Shore A. Hardness was determined according to ASTM D 2240.

Example 11

Curing of Acrylate-Terminated Sulfur-Containing Polymer

The curing reaction was carried out in a 100-g plastic container equipped with a lid. The acrylate-terminated sulfur-containing polymer of Example 6 (40.8 g) and IRGACURE® 2022 (0.2 g, 0.5% by weight) were mixed by hand in the container. The container was then placed in a speed mixer (DAC 600 FVZ) and mixed for 1 min at 2,300 rpm. The polymer was poured over a circular (5 in-diameter) metal lid (pre-treated with Valspar Mold Release 225), and placed under ultraviolet (UV) radiation for 30 sec, after which time the polymer had completely cured. A Super Six curing unit (Fusion Systems Inc.) was used to provide the UV radiation. The curing unit was equipped with a 300 W H-bulb, which produced UV wavelengths ranging from 200 nm to 450 nm A total dosage of 3.103 J/cm$^2$ UV energy, measured using a UV power puck (EIT, Inc., Sterling, Va.) was applied to the polymer composition. A ½ inch-thick disc of cured polymer was obtained. The hardness of the polymer was measured with a durometer to be 54 Shore A. Hardness was determined according to ASTM D 2240.

Example 12

Curing of TMI-Terminated Sulfur-Containing Polymer

The curing reaction was performed in a 100-g plastic container equipped with a lid. The TMI-terminated sulfur-containing polymer described in Example 7 (40.8 g) and IRGACURE® 2022 (0.2 g, 0.5% by weight) were mixed by hand in the container. The container was then placed in a speed mixer (DAC 600 FVZ) and mixed for 1 min at 2,300 rpm. The polymer was poured over a circular (5 inch-diameter) metal lid (pre-treated with Valspar Mold Release 225), and placed under UV light for 60 sec. A Super Six curing unit (Fusion Systems Inc.) was used to provide the UV radiation. The curing unit was equipped with a 300 W H-bulb, which produced UV wavelengths ranging from 200 nm to 450 nm A total dosage of 3.103 J/cm$^2$ UV energy, measured using a UV power puck (EIT, Inc., Sterling, Va.) was applied to the polymer composition. A 1 mm-thick disc of cured polymer was obtained.

Example 13

Curing of TMI-Terminated Sulfur-Containing Polymer

The curing reaction was performed in a 100-g plastic container equipped with a lid. The TMI-terminated sulfur-containing polymer described in Example 8 (40.8 g) and IRGACURE® 2022 (0.2 g, 0.5% by weight) were mixed by hand in the container. The container was then placed in a speed mixer (DAC 600 FVZ) and mixed for 1 min at 2,300 rpm. The polymer was poured over a circular (5 inch-diameter) metal lid (pre-treated with Valspar Mold Release 225), and placed under UV light for 60 sec. A Super Six curing unit (Fusion Systems Inc.) was used to provide the UV radiation. The curing unit was equipped with a 300 W H-bulb, which produced UV wavelengths ranging from 200 nm to 450 nm A total dosage of 3.103 J/cm$^2$ UV energy, measured using a UV power puck (EIT, Inc., Sterling, Va.) was applied to the polymer composition. A 1 mm-thick disc of cured polymer was obtained.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A terminal-modified sulfur-containing polymer comprising the reaction products of reactants comprising:
(a) a sulfur-containing polymer of Formula (I);

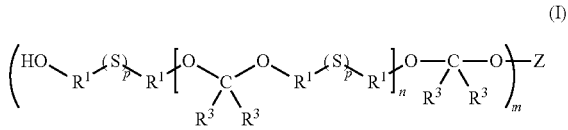

wherein:
each n is an integer selected from 1 to 50;
m is an integer selected from 3 to 6;
each p is 1;
each $R^1$ is $C_{2-6}$ alkanediyl;
each $R^3$ is selected from hydrogen and $C_{1-4}$ alkyl; and
Z represents the core of an m-valent parent polyol $Z(OH)_m$; and
(b) a compound comprising a terminal silyl group and a group that is reactive with the hydroxyl groups of the sulfur-containing polymer of Formula (I).

2. The terminal-modified sulfur-containing polymer of claim 1, wherein,
each $R^1$ is independently selected from ethane-1,2-diyl; and
each $R^3$ is hydrogen.

3. The terminal-modified sulfur-containing polymer of claim 1, wherein the sulfur-containing polymer of Formula (I) comprises the reaction products of:
(i) a sulfur-containing diol; and
(ii) a reactant selected from an aldehyde, ketone, and a combination thereof.

4. The terminal-modified sulfur-containing polymer of claim 3, wherein the sulfur-containing diol is selected from 2,2'-thiodiethanol, 3,3'-thiobis(propan-1-ol), 4,4'-thiobis(butan-1-ol), and a combination of any of the foregoing.

5. The terminal-modified sulfur-containing polymer of claim 3, wherein (ii) is an aldehyde and comprises formaldehyde.

6. The terminal-modified sulfur-containing polymer of claim 3, wherein,
the sulfur-containing diol comprises 2,2'-thiodiethanol; and
the reactant comprises formaldehyde.

7. The terminal-modified sulfur-containing polymer of claim 1, wherein the sulfur-containing polymer of Formula (I) has a hydroxyl number from 10 to 100.

8. The terminal-modified sulfur-containing polymer of claim 1, wherein,
each $R^1$ is the same and is selected from ethane-1,2-diyl and propane-1,3-diyl; and
each $R^3$ is independently selected from hydrogen, methyl, and ethyl.

9. The terminal-modified sulfur-containing polymer of claim 1, wherein n is an integer selected from 7 to 30.

10. The terminal-modified sulfur-containing polymer of claim 1, wherein the compound comprising a terminal silyl group is an isocyanatoalkylalkoxysilane.

11. The terminal-modified sulfur-containing polymer of claim 1, wherein the compound comprising a terminal silyl group comprises isocyanatopropylmethoxysilane, isocyanatopropylmethyldimethoxysilane, isocyanatopropylmethyldiethoxysilane, isocyanatopropyltriethoxysilane, isocyanatopropyltriisopropoxysilane, isocyanatopropylmethyldiisopropoxysilane, isocyanatoneohexyltrimethoxysilane, isocyanatoneohexyldimethoxysilane, isocyanatoneohexyldiethoxysilane, isocyanatoneohexyltriethoxysilane, isocyanatoneohexyltriisopropoxysilane, isocyanatoneohexyldiisopropoxysilane, isocyanatoisoamyltrimethoxysilane, isocyanatoisoamyldimethoxysilane, isocyanatoisoamylmethylsilane, isocyanatoisoamylmethyldiethoxysilane, isocyanatoisoamyltriethoxysilane, isocyanatoisoamyltriisopropoxysilane, isocyanatoisoamylmethyldiisopropoxysilane, or a combination of any of the foregoing.

12. The terminal-modified sulfur-containing polymer of claim 1, wherein the compound comprising a terminal silyl group comprises 3-isocyanatopropyltriethoxysilane or 3-isocyanatopropyltrimethoxysilane.

13. The terminal-modified sulfur-containing polymer of claim 1, wherein,
n is an integer selected from 2 to 50;
each p is 1;
each $R^1$ is independently selected from ethane-1,2-diyl; and
each $R^3$ is hydrogen.

14. The terminal-modified sulfur-containing polymer of claim 1, wherein Z is selected from a moiety of Formula (1) and a moiety of Formula (2):

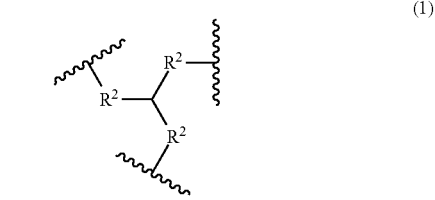

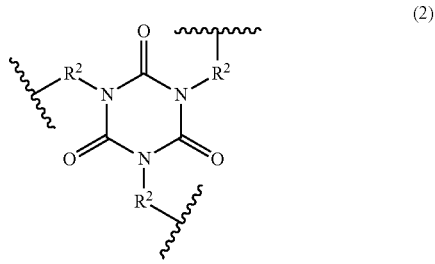

wherein each $R^2$ is independently $C_{1-6}$ alkanediyl.

15. A terminal-modified sulfur-containing polymer of Formula (II):

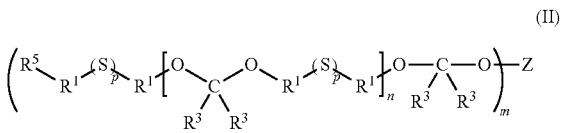

wherein:
each n is an integer selected from 1 to 50;
m is an integer selected from 3 to 6;
each p is 1;
each $R^1$ is $C_{2-6}$ alkanediyl;
each $R^3$ is selected from hydrogen and $C_{1-4}$ alkyl;
each $R^5$ is independently selected from a silyl-terminated group; and Z represents the core of an m-valent parent polyol Z(OH)$_m$.

16. The terminal-modified sulfur-containing polymer of claim 15, wherein each R$^5$ is selected from a silyl-terminated group of Formula (f) and Formula (g):

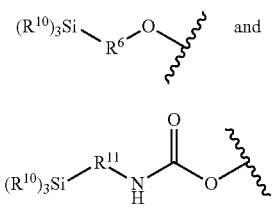

wherein:
 each R$^6$ is derived from an ethylenically unsaturated monoisocyanate;
 each R$^{10}$ is independently selected from C$_{1-6}$ alkyl, C$_{1-6}$ alkoxy, C$_{5-6}$ cycloalkyl, C$_{6-12}$ cycloalkylalkyl, phenyl, and C$_{7-12}$ phenylalkyl; wherein at least one R$^{10}$ is C$_{1-6}$ alkoxy; and
 each R$^{11}$ is C$_{1-6}$ alkanediyl.

17. The terminal-modified sulfur-containing polymer of claim 16, wherein,
 R$^{11}$ is selected from methane-diyl, ethane-1,2-diyl, and propane-1,2-diyl; and
 each R$^{10}$ is selected from methoxy, ethoxy and propoxy.

18. A composition comprising the terminal-modified sulfur-containing polymer of claim 1.

19. The composition of claim 18, formulated as a sealant.

20. A part sealed with the composition of claim 19.

21. A composition comprising the terminal-modified sulfur-containing polymer of claim 15.

22. The composition of claim 21, formulated as a sealant.

23. A part sealed with the composition of claim 22.

* * * * *